(12) United States Patent
Ogawa et al.

(10) Patent No.: US 9,337,432 B2
(45) Date of Patent: May 10, 2016

(54) ORGANIC ELECTROLUMINESCENT ELEMENT

(75) Inventors: Junya Ogawa, Kitakyushu (JP); Takahiro Kai, Kitakyushu (JP); Megumi Matsumoto, Kitakyushu (JP)

(73) Assignee: NIPPON STEEL & SUMKIN CHEMICAL CO., LTD., Tokyo (JP)

( * ) Notice: Subject to any disclaimer, the term of this patent is extended or adjusted under 35 U.S.C. 154(b) by 419 days.

(21) Appl. No.: 13/990,511

(22) PCT Filed: Nov. 28, 2011

(86) PCT No.: PCT/JP2011/077384
§ 371 (c)(1),
(2), (4) Date: May 30, 2013

(87) PCT Pub. No.: WO2012/077520
PCT Pub. Date: Jun. 14, 2012

(65) Prior Publication Data
US 2013/0248845 A1    Sep. 26, 2013

(30) Foreign Application Priority Data
Dec. 9, 2010    (JP) .................................. 2010-274334

(51) Int. Cl.
*H01L 51/50* (2006.01)
*H01L 51/00* (2006.01)
(Continued)

(52) U.S. Cl.
CPC .......... *H01L 51/0072* (2013.01); *C07D 209/82* (2013.01); *C07D 401/04* (2013.01); *C07D 403/04* (2013.01); *C07D 405/04* (2013.01); *C07D 409/04* (2013.01); *C09K 11/06* (2013.01); *H01L 51/0071* (2013.01); *H05B 33/14* (2013.01); *C09K 2211/1011* (2013.01); *C09K 2211/1029* (2013.01);
(Continued)

(58) Field of Classification Search
None
See application file for complete search history.

(56) References Cited

U.S. PATENT DOCUMENTS 6,451,461 B2    9/2002    Lee et al.
7,279,704 B2 *  10/2007    Walters et al. .................. 257/40
(Continued)

FOREIGN PATENT DOCUMENTS

WO    WO-2009/086028 A2    7/2009

OTHER PUBLICATIONS

International Search Report for the Application No. PCT/JP2011/077384 mailed Jan. 24, 2012.
(Continued)

*Primary Examiner* — Gregory Clark
(74) *Attorney, Agent, or Firm* — Cheng Law Goup, PLLC

(57) ABSTRACT

Provided is an organic electroluminescent device (organic EL device) which exhibits improved luminous efficiency, ensures sufficient driving stability, and has a simple configuration. The organic electroluminescent element includes an anode, a plurality of organic layers, and a cathode laminated on a substrate, and contains a carbazole compound represented by the general formula (1) in at least one layer selected from the group consisting of a emitting layer, a hole-transporting layer, and an electron-blocking layer. In general formula (1), L represents an m-valent aromatic hydrocarbon group or aromatic heterocyclic group, R's each represent hydrogen, an alkyl group, or a cycloalkyl group, m represents an integer of 1 to 3, and n's each represent an integer of 1 to 4, provided that at least one n represents an integer of 2 to 4, and at least one specific structure represented by the formula (1a) is present in the formula.

9 Claims, 3 Drawing Sheets

(51) Int. Cl.
  *C07D 209/82* (2006.01)
  *C07D 401/04* (2006.01)
  *C07D 403/04* (2006.01)
  *C07D 405/04* (2006.01)
  *C07D 409/04* (2006.01)
  *C09K 11/06* (2006.01)
  *H05B 33/14* (2006.01)

(52) U.S. Cl.
  CPC .......... *C09K 2211/1044* (2013.01); *C09K 2211/1059* (2013.01); *C09K 2211/1088* (2013.01); *C09K 2211/1092* (2013.01); *H01L 51/0073* (2013.01); *H01L 51/5012* (2013.01); *H01L 51/5056* (2013.01); *H01L 51/5096* (2013.01)

(56) References Cited

U.S. PATENT DOCUMENTS

| | | |
|---|---|---|
| 2006/0054861 A1 | 3/2006 | Ionkin et al. |
| 2010/0145067 A1 | 6/2010 | Yokota et al. |
| 2010/0187984 A1* | 7/2010 | Lin et al. ................. 313/504 |
| 2012/0205636 A1 | 8/2012 | Kim et al. |
| 2012/0223276 A1 | 9/2012 | Parham et al. |
| 2012/0235136 A1 | 9/2012 | Ogawa et al. |

OTHER PUBLICATIONS

International Preliminary Report on Patentability for Application No. PCT/JP2011/077384 mailed Jun. 20, 2013.

* cited by examiner

ORGANIC ELECTROLUMINESCENT ELEMENT

TECHNICAL FIELD

The present invention relates to an organic electroluminescent device containing a carbazole compound having a specific structure, and specifically, to a thin-film-type device that emits light when an electric field is applied to a emitting layer formed of an organic compound.

BACKGROUND ART

In general, an organic electroluminescent device (hereinafter referred to as organic EL device) is constructed of a emitting layer and a pair of counter electrodes interposing the emitting layer therebetween in its simplest structure. That is, the organic EL device uses the phenomenon that, when an electric field is applied between both the electrodes, electrons are injected from a cathode and holes are injected from an anode, and each electron and each hole recombine in the emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a emitting layer formed of an 8-hydrozyquinoline aluminum complex (hereinafter referred to as Alq3) are provided between electrodes as thin films, resulting in a significant improvement in luminous efficiency, compared with conventional devices in which a single crystal of anthracene molecules or the like is used. Thus, the development of the above-mentioned organic EL device has been promoted in order to accomplish its practical application to a high-performance flat panel having features such as self-luminescence and rapid response.

Further, studies have been, made on using phosphorescent light rather than fluorescent light as an attempt to raise the luminous efficiency of a device. Many kinds of devices including the above-mentioned device in which a hole-transporting layer formed of an aromatic diamine and a emitting layer formed of Alq3 are provided emit light by using fluorescent light emission. However, by using phosphorescent light emission, that is, by using light emission from a triplet excited state, luminous efficiency is expected to be improved by about three times to four times, compared with the case of using conventional devices in which fluorescent light (singlet) is used. In order to accomplish this purpose, studies have been made on adopting a coumarin derivative or a benzophenone derivative as a emitting layer, but extremely low luminance has only been provided. Further, studies have been made on using a europium complex as an attempt to use a triplet state, but highly efficient light emission has not been accomplished. In recent years, many studies centered on an organic metal complex such as an iridium complex have been made, as described in Patent Literature 1, for the purpose of attaining the high efficiency and long lifetime of light emission.

CITATION LIST

Patent Literature

[PTL 1] JP 2003-515897 T
[PTL 2] JP 2001-313178 A
[PTL 3] US 2006/054861 A1
[PTL 4] JP 2008-195841 A
[PTL 5] WO 2009/086028 A1

In order to obtain high luminous efficiency, host materials that are used with the dopant materials described above play an important role. Typical examples of the host materials proposed include 4,4'-bis(9-carbazolyl)biphenyl (hereinafter referred to as CBP) as a carbazole compound introduced in Patent Literature 2. When CBP is used as a host material for a green phosphorescent light-emitting material typified by a tris(2-phenylpyridine)iridium complex (hereinafter referred to as $Ir(ppy)_3$), the charge balance is disturbed because CBP has the characteristic of facilitating the delivery of holes and not facilitating the delivery of electrons. Thus, excessively delivered holes flow out into an electron-transporting layer side, with the result that the luminous efficiency from $Ir(ppy)_3$ lowers.

In order to provide high luminous efficiency to an organic EL device, it is necessary to use a host material, which has high triplet excitation energy, and is striking a good balance in both charge (hole and electron)—injecting/transporting property. Further desired is a compound for the material, which has electrochemical stability, has high heat resistance, and has excellent amorphous stability, and hence further improvement, has been demanded.

Patent Literature 3 discloses the carbazole compound shown below. However, the literature merely discloses an organic EL device using a compound substituted with the 4-position of carbazole, and does not disclose the usefulness of an organic EL device using a compound obtained by substituting the 4-position of a carbazole compound with the 9-position of carbazole.

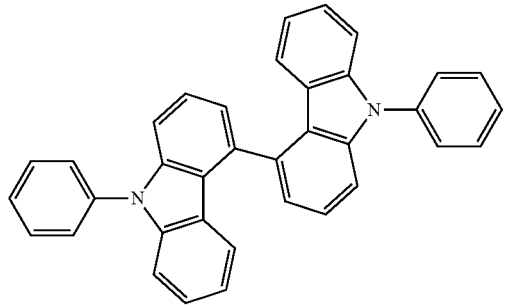 [SMILES: c1ccc(-n2c3ccccc3c3c(-c4cccc5c4c4ccccc4n5-c4ccccc4)cccc32)cc1]

In addition, Patent Literature 4 discloses an organic EL device using the compound as shown below.

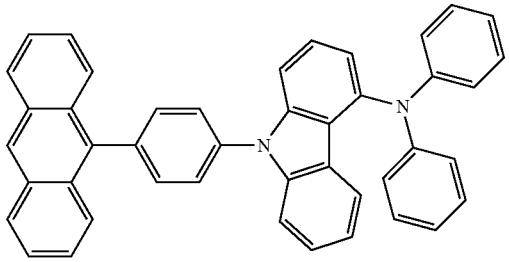 [SMILES: c1ccc(N(c2ccccc2)c2cccc3c2c2ccccc2n3-c2ccc(-c3c4ccccc4cc4ccccc34)cc2)cc1]

However, the literature merely discloses the usefulness of a compound obtained by substituting the 4-position of carbazole with diphenylamine as an organic EL device, and docs not disclose the usefulness of an organic EL device using a compound obtained by substituting the 4-position with carbazole.

In addition, Patent Literature 5 discloses the compound as shown below and an organic EL device using the compound.

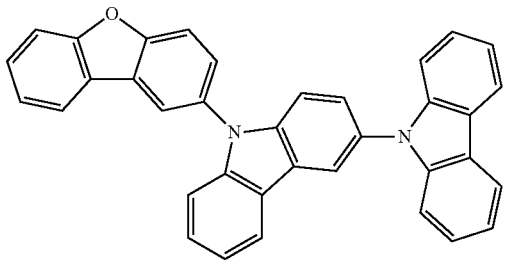 [SMILES: c1ccc2c(c1)oc1ccc(-n3c4ccccc4c4cc(-n5c6ccccc6c6ccccc65)ccc43)cc12]

However, the literature merely discloses the usefulness of a compound obtained by substituting the 3-position of a carbazole compound with carbazole as an organic EL device, and does not disclose the usefulness of an organic EL device using a compound obtained by substituting the 4-position with carbazole.

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device, which has high efficiency, has high driving stability, and is practically useful and a compound suitable for the organic EL device.

The inventors of the present invention have made intensive studies and have consequently found that, when a carbazole compound having a specific skeleton is used in an organic EL device, the organic EL device exhibits excellent characteristics. As a result, the present invention has been completed.

The present invention relates to an organic electroluminescent device, including an anode, a plurality of organic layers, and a cathode laminated on a substrate, in which the organic electroluminescent device contains a carbazole compound represented by the general formula (1) in at least one layer selected from the group consisting of a emitting layer, a hole-transporting layer, and an electron-blocking layer:

(1)

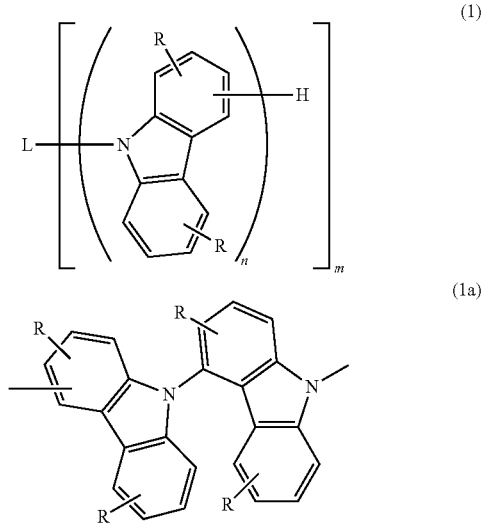

(1a)

where L represents an m-valent aromatic hydrocarbon group having 6 to 30 carbon atoms in total or aromatic heterocyclic group having 3 to 30 carbon atoms in total, but does not represent a carbazole ring-containing group, m represents an integer of 1 to 3, and n's each independently represent an integer of 1 to 4, provided that at least one n represents an integer of 2 to 4, and at least one specific structure represented by the formula (1a) is present in the formula, in the general formula (1) and the formula (1a), R's each independently represent hydrogen, an alkyl group having 1 to 10 carbon atoms, or a cycloalkyl group having 3 to 11 carbon atoms.

In the general formula (1), it is preferred that m represent an integer of 1 or 2, n's each independently represent an integer of 1 to 3, and at least one n represent an integer of 2 or 3.

In addition, in the general formula (1), it is preferred that all specific structures between carbazole rings include specific structures represented by the formula (1a) or by the formula (1a) and the following formula (1b):

(1b)

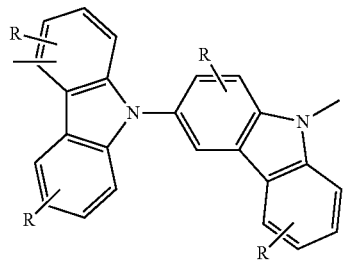

where R's each have the same meaning as that in the formula (1a).

In the general formula (1), L preferably represents an m-valent group produced by removing m hydrogen atoms from any one of the formulae (2) to (5):

(2)

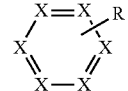

(3)

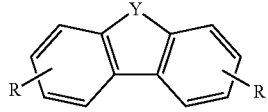

(4)

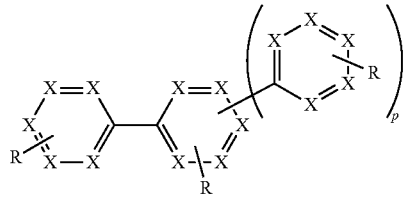

(5)

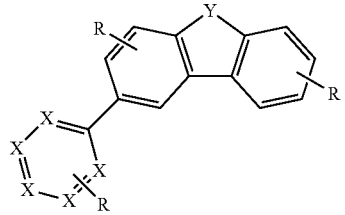

in the formulae (2) to (5), X's each independently represent CH or nitrogen and R's each independently represent hydrogen, an alkyl group having 1 to 10 carbon atoms, or a cycloalkyl group having 3 to 11 carbon atom, in each of the formulae (3) and (5), Y represents oxygen or sulfur, and in the formula (A), p represents an integer of 0 to 2.

In the general formula (1), L more preferably represents an m-valent group produced by removing in hydrogen atoms from any one of the formulae (2), (3), and (4).

In addition, in the general formula (1), it is preferred that a sum of n's be an integer of 2 to 6.

The present invention also relates to the above-mentioned organic electroluminescent device, in which the organic layer containing the carbazole compound includes a emitting layer containing a phosphorescent light-emitting dopant.

DESCRIPTION OF EMBODIMENTS

Figure 1:
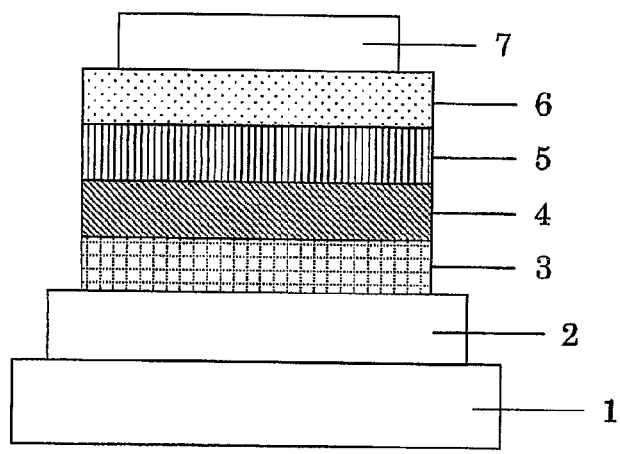
[FIG. 1] A sectional view illustrating an example of the structure of an organic EL device.

An organic electroluminescent device of the present invention contains, in its organic layers, a carbazole compound represented by the general formula (1) (hereinafter sometimes referred to as "compound represented by the general formula (1)"), The carbazole compound exerts such excellent effects as described above probably because the compound has a 4-(9-carbazolyl) carbazole structure.

In the general formula (1), L represents an m-valent group produced by removing m hydrogen atoms from an aromatic hydrocarbon having 6 to 30 carbon atoms in total or an aromatic heterocyclic compound having 3 to 30 carbon atoms in total, L preferably represents an m-valent group produced by removing m hydrogen atoms from an aromatic hydrocarbon or aromatic heterocyclic compound having 6 to 18 carbon atoms in total. In this case, L does not represent a carbazole ring-containing group. The term "carbazole ring-containing group" as used herein refers to an m-valent group produced by removing m hydrogen atoms from a substituted or unsubstituted carbazole. Specifically, the term refers to an m-valent group produced by removing m hydrogen atoms from N or C constituting a carbazole ring.

Specific examples of the aromatic hydrocarbon group or the aromatic heterocyclic group include benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxanthrene, dibenzofuran, perixanthenoxanthene, thiophene, thioxanthene, thianthrene, phenoxathiin, thionaphthene, isothianaphtene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, benzisothiazole, and an aromatic compound in which a plurality of such aromatic rings are linked to each other.

It should be noted that in the case of the aromatic compound in which a plurality of aromatic rings are linked to each other, the number of the aromatic rings to be linked to each other is preferably 2 to 10, more preferably 2 to 7, and the aromatic rings to be linked to each other may be identical to or different from each other. In that case, in the formula (1), the bonding position to be bonded to m carbazolyl groups is not limited, and may be a ring at a terminal portion of linked aromatic rings or a ring at the central portion thereof. Herein, the term "aromatic ring" is meant to collectively refer to an aromatic hydrocarbon ring and an aromatic heterocycle. In addition, when the linked aromatic rings include at least one heterocycle, the linked aromatic rings are included in the aromatic heterocycle.

Here, when the m-valent group produced by the aromatic compound in which a plurality of aromatic rings are linked to each other is a monovalent group, the m-valent group is, for example, represented by any one of the following formulae.

(11)

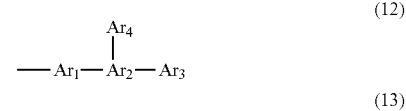
(12)

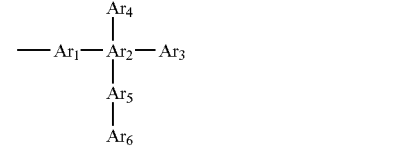
(13)

In the formulae (11) to (13), $Ar_1$ to $Ar_6$ each represent a substituted or non-substituted aromatic ring.

Specific examples of the group produced by the linking of a plurality of aromatic rings include monovalent groups each produced by removing hydrogen from, for example, biphenyl, terphenyl, bipyridine, bipyrimidine, bitriazine, terpyridine, bistriazylbenzene, phenylterphenyl, binaphthalene, phenylpyridine, diphenylpyridine, phenylpyrimidine, diphenylpyrimidine, phenyltriazine, diphenyltriazine, phenylnaphthalene, or diphenylnapthalene.

In the general formula (1), a preferred embodiment of L is, for example, an m-valent group produced from an aromatic compound represented by any one of the formulae (2) to (5), preferably any one of the formulae (2) to (4). Such m-valent group is an m-valent group produced by removing m hydrogen atoms from carbon forming a ring appearing in any one of the formulae (2) to (5), and when m represents 2 or more, the hydrogen atoms may be removed from the same ring or may be removed from different rings.

In the formulae (2) to (5), X's each independently represent methine or nitrogen. Of X's constituting each six-membered ring, 0 to 3 X's each preferably represent nitrogen and all X's each more preferably represent methine. In each of the formulae (3) and (5), Y represents oxygen or sulfur. In the formula (4), p, which represents an integer of 0 to 2, preferably represents 0 or 1.

In the general formula (1), specific examples of the aromatic compound providing the preferred embodiment of L include benzene, pyridine, pyrazine, pyrimidine, pyridazine, triazine, dibenzofuran, dibenzothiophene, biphenyl, terphenyl, bipyridine, bipyrimidine, bitriazine, terpyridine, bistriazylbenzene, phenylpyridine, diphenylpyridine, phenylpyrimidine, diphenylpyrimidine, phenyltriazine, diphenyltriazine, phenyldibenzofuran, phenyldibenzothiophene, dibenzofuranylpyridine, and dibenzothienylpyridine. More preferred examples thereof include benzene, dibenzofuran, dibenzothiophene, biphenyl, terphenyl, bistriazylbenzene, phenyldibenzofuran, and phenyldibenzothiophene.

In the general formula (1), m represents an integer of 1 to 3. m preferably represents 1 or 2, and m more preferably represents 1.

In the general formula (1), n's each independently represent an integer of 1 to 4. n's each preferably represent 1 to 3. However, at least one n represents an integer of 2 to 4 and at least one specific structure represented by the formula (1a) is present in the formula. All specific structures between carbazole rings are preferably specific structures represented by the formula (1a) or by the formula (1a) and the formula (1b). Herein, the term "carbazole ring" refers to a fused ring having 3 rings appearing in the general formula (1). The sum of n's (total number of the carbazole rings), which is an integer of 2 to 12, is preferably 2 to 9, more preferably 2 to 6.

The general formula (1) needs to have one or more specific structures represented by the formula (1a). When m represents 2 or more and n's each represent 2 or more, all specific structures are preferably specific structures represented by the formula (1a) or both specific structures represented by the formula (1a) and the formula (1b). In this context, when n represents 3 or more, two or more specific structures are present and each of the structures is preferably such specific structure as described above. It should be noted that when one carbazole ring in each of the specific structures represented by the formula (1a) and the formula (1b) is a terminal carbazole ring, it is preferred that one bond foe bonded to hydrogen and N- be bonded to L or any other carbazole ring, In the general formula (1), the formulae (2) to (5), and the formulae (1a) and (1b), R's each independently represent hydrogen, an alkyl group having 1 to 10 carbon atoms, or a cycloalkyl. group having 3 to 11 carbon atoms, R's each preferably represent hydrogen, an alkyl group having 1 to 8 carbon atoms, or a cycloalkyl group having 3 to 8 carbon atoms, and each more preferably represent hydrogen, an alkyl group having 1 to 4 carbon atoms, or a cycloalkyl group having 5 to 7 carbon atoms.

Specific examples of the alkyl group include a methyl group, an ethyl group, a propyl group, a butyl group, a pentyl group, a hexyl group, a heptyl group, an octyl group, a nonyl group, and a decyl group. Preferred examples thereof include a methyl group, an ethyl group, a propyl group, a butyl group, a pentyl group, a hexyl group, a heptyl group, and an octyl group. The alkyl group may be linear or branched.

Specific examples of the cycloalkyl group include a cyclopropyl group, a cyclobutyl group, a cyclopentyl group, a cyclohexyl group, a cycloheptyl group, a cyclooctyl group, and a methylcyclohexyl group. Preferred examples thereof include a cyclohexyl group and a methylcyclohexyl group.

The symbols and formulae identical to one another in the general formula (1) and the formulae (2) to (5), and the formulae (1a) and (1b) are interpreted as having the same meaning unless otherwise stated.

The carbazole compound of the present invention can be synthesized from a carbazole derivative whose 4-position has been substituted with a halogen atom as a starting material by employing a known approach after selecting raw materials in accordance with the structure of the target compound.

For example, a 4-fluorocarbazole skeleton of a carbazole derivative whose 4-position has been substituted with a fluorine atom can be synthesized by the following reaction formula with reference to a synthesis example described in Journal of Organic Chemistry, 2008, No. 73, p 7603-p 7610.

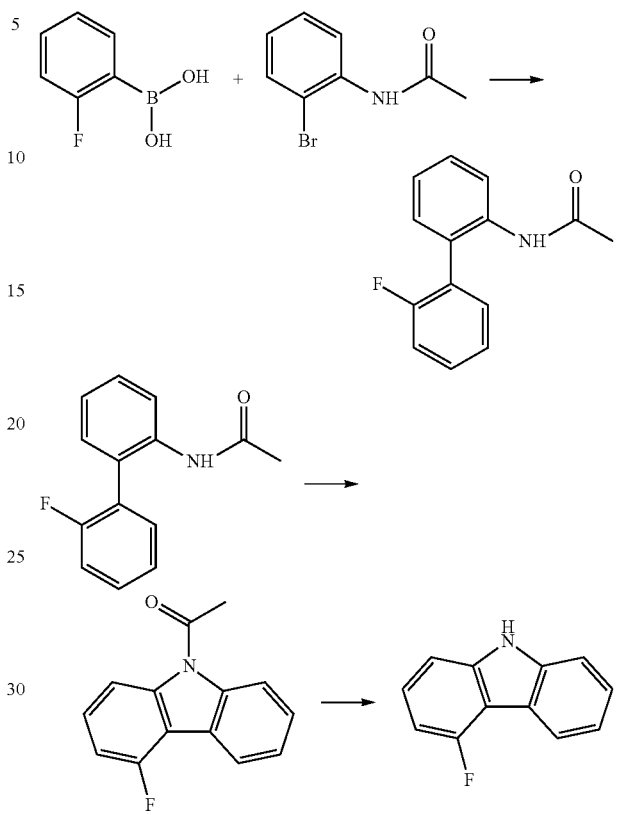

The compound represented by the general formula (1) can be synthesized by substituting hydrogen on nitrogen of a carbazole compound obtained by the foregoing reaction formula with the corresponding substituent through a coupling reaction such as the Ullmann reaction.

Specific examples of the carbazole compound represented by the general formula (1) are shown below. However, a material to be used for an organic electroluminescent device of the present invention is not limited thereto.

1-1

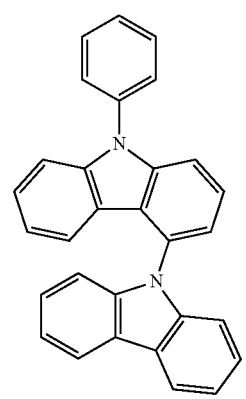

1-2
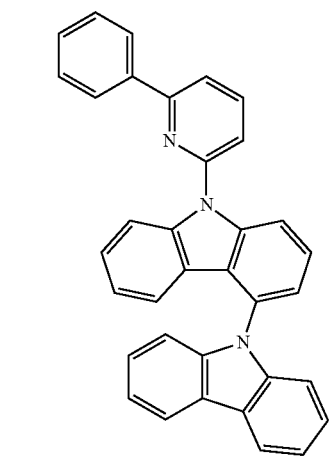
1-3
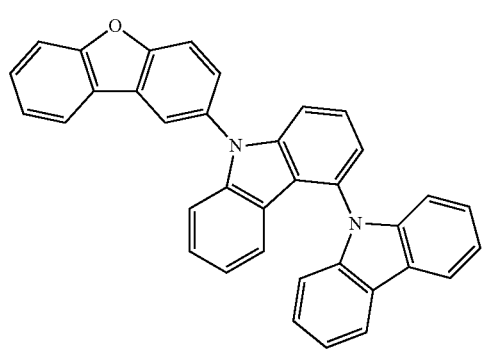
1-4
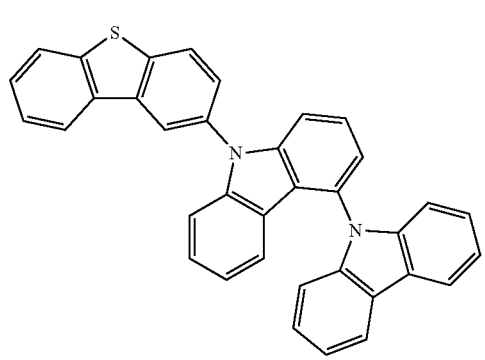
1-5
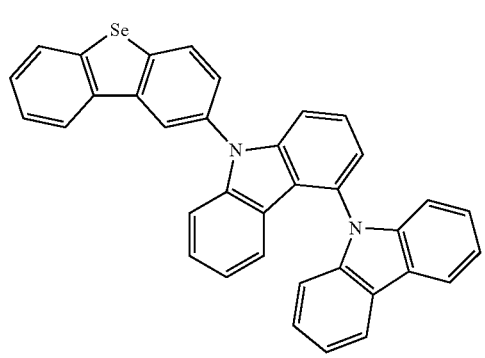
1-6
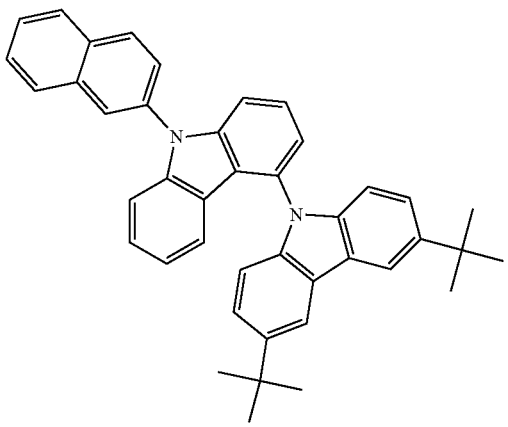
1-7
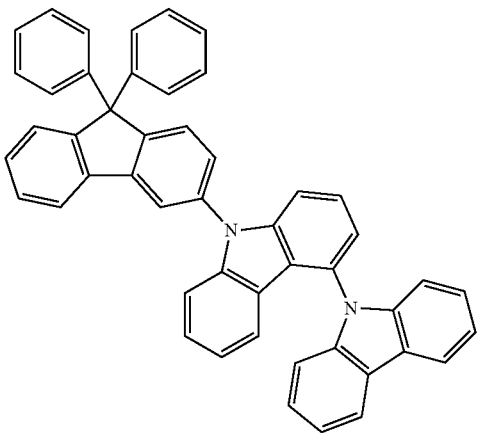
1-8
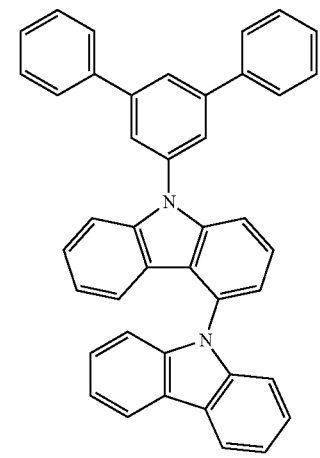

1-9
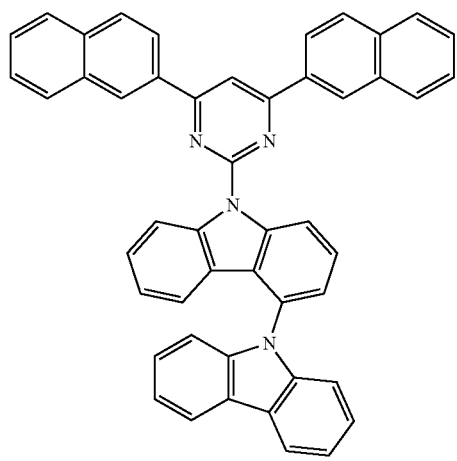
1-10
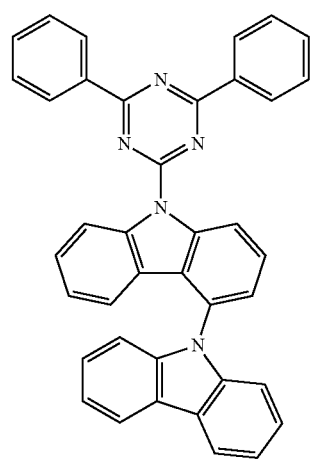
1-11
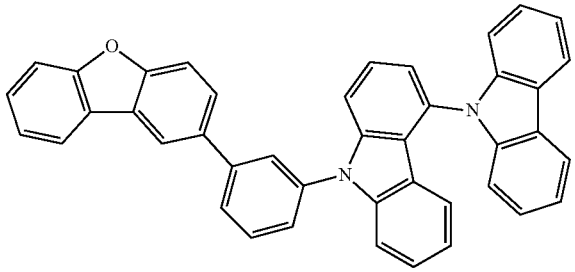
1-12
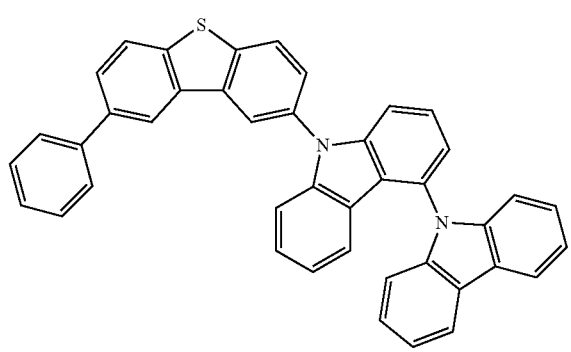
1-13
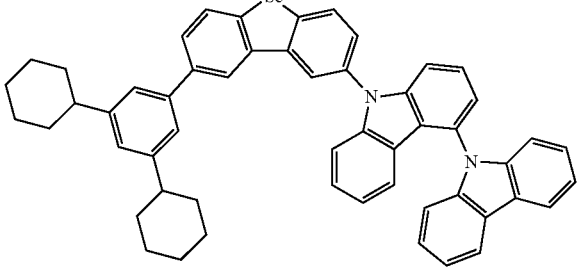
1-14
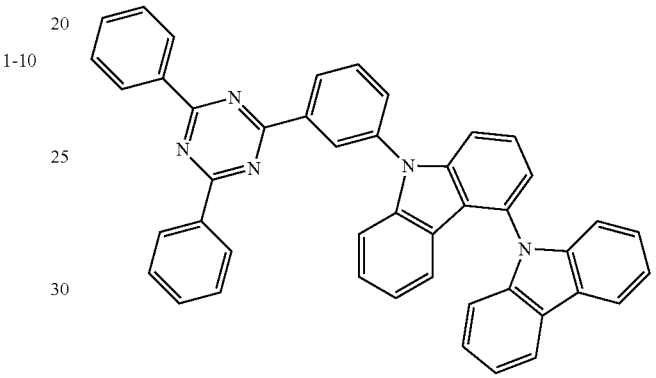
1-15
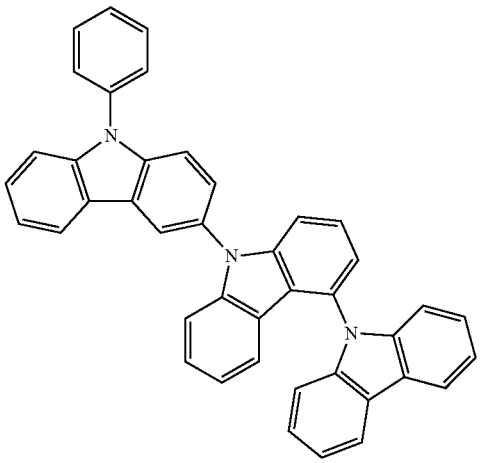
1-16
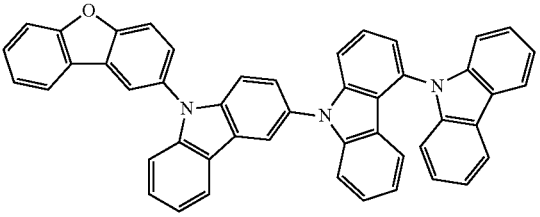

1-17
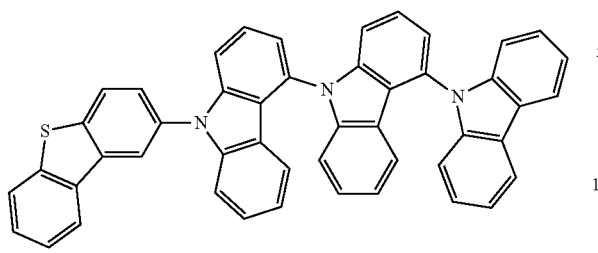
1-18
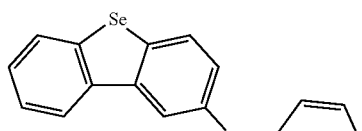
1-19
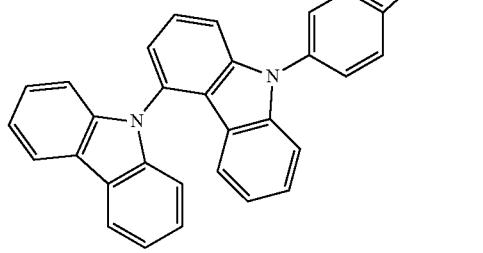
1-20
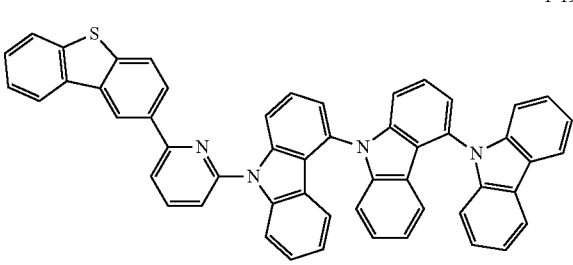
1-21
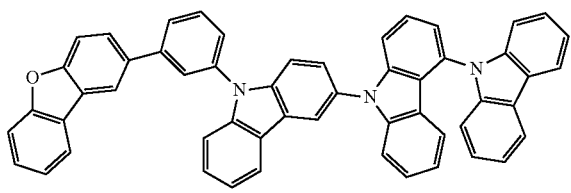
1-22
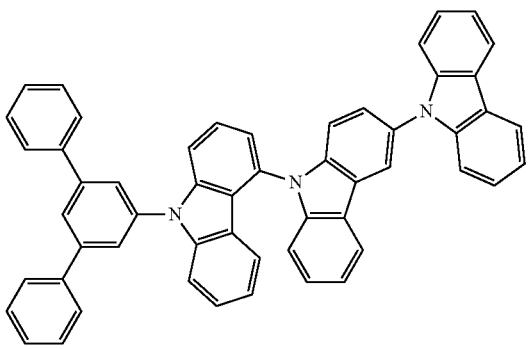
1-23
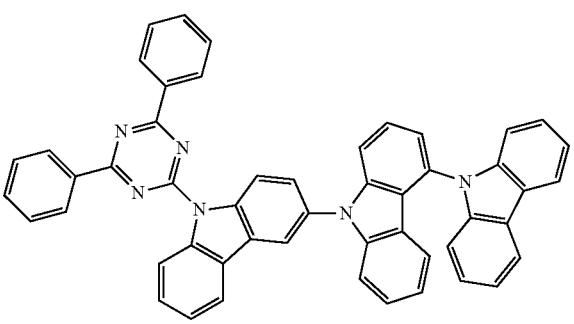
1-24
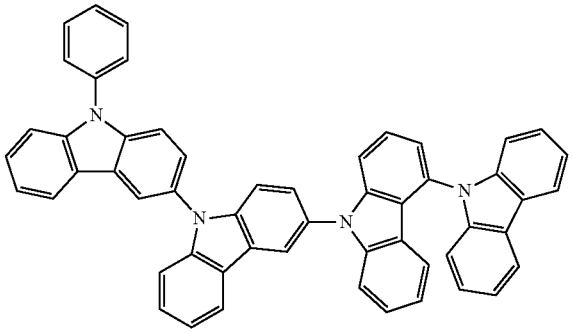
1-25
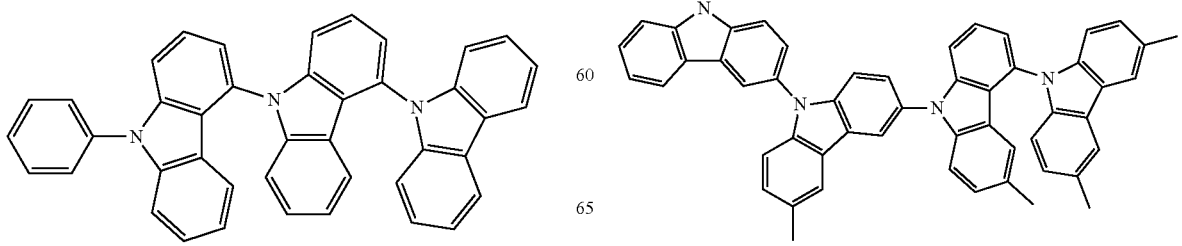

-continued
1-26
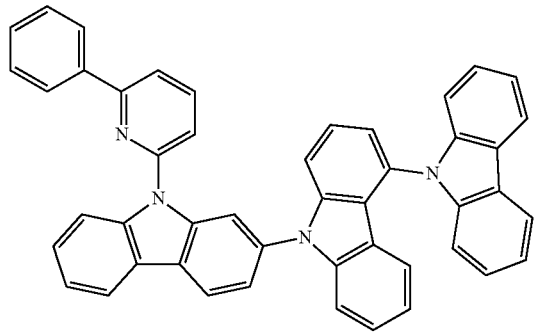
1-27
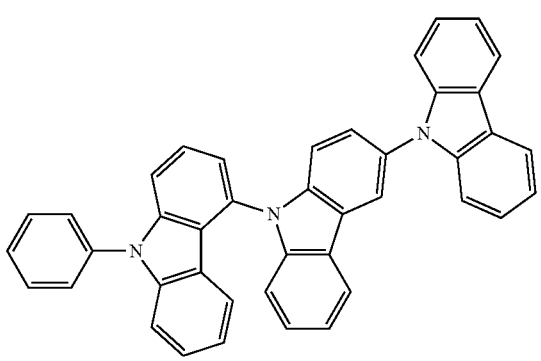
1-28
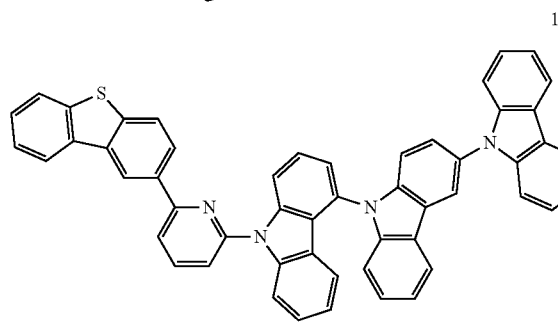
1-29
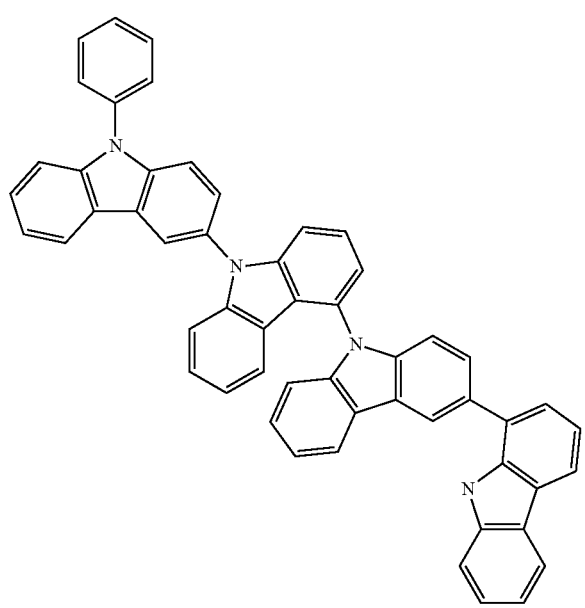
-continued
1-30
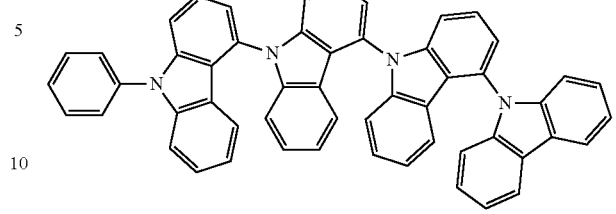
1-30
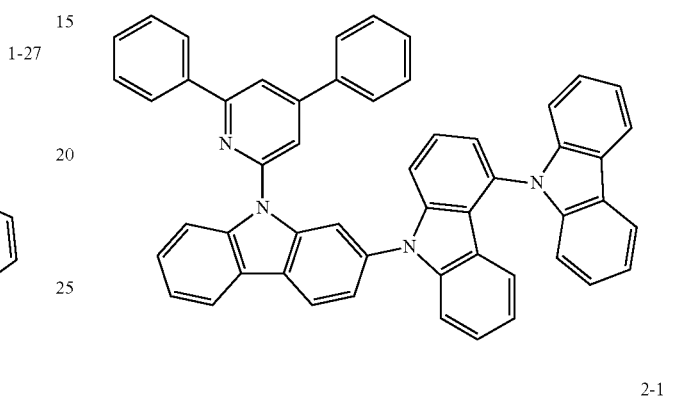
2-1
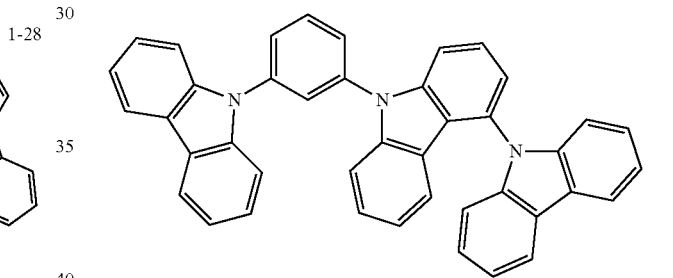
2-2
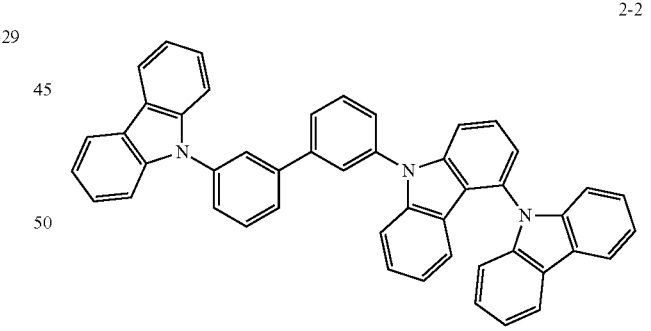
2-3
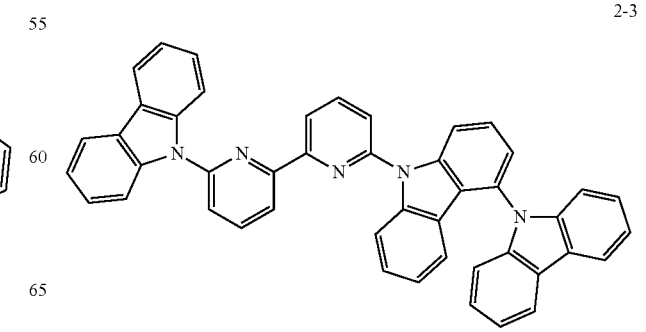

-continued
2-4
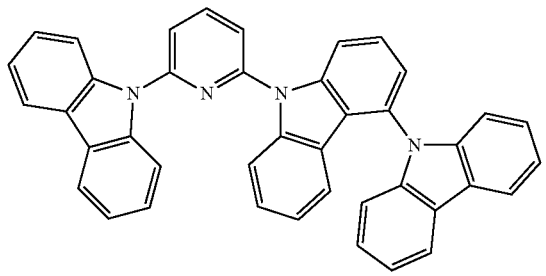
2-5
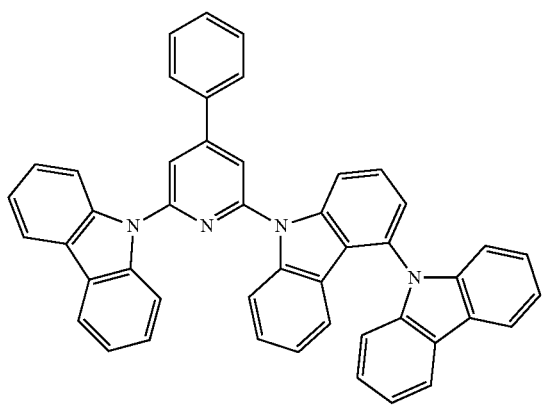
2-6
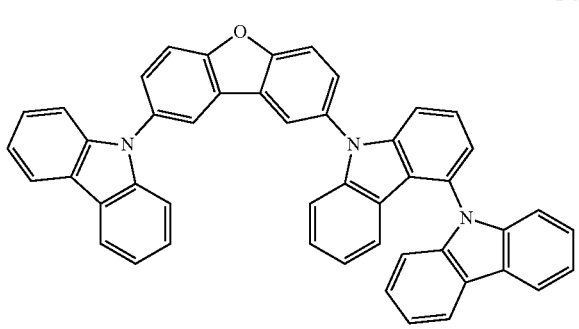
2-7
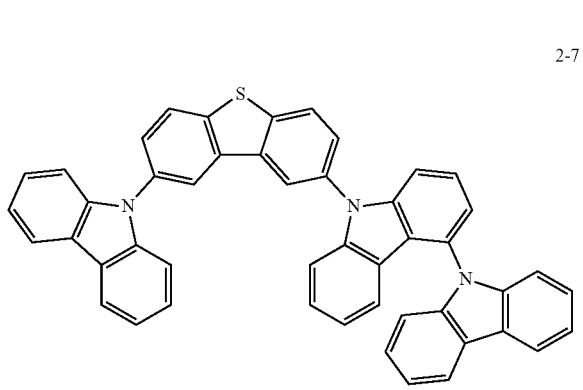
-continued
2-8
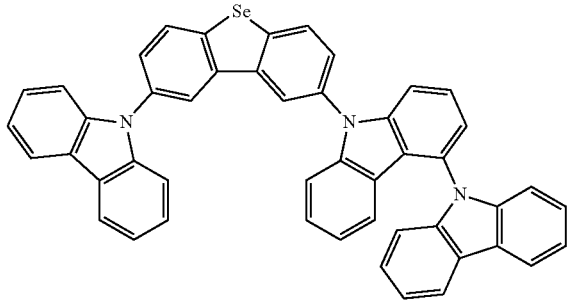
2-9
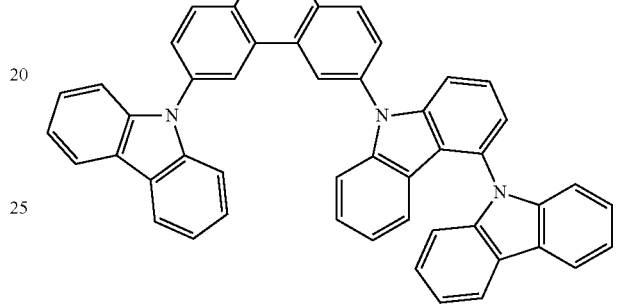
2-10
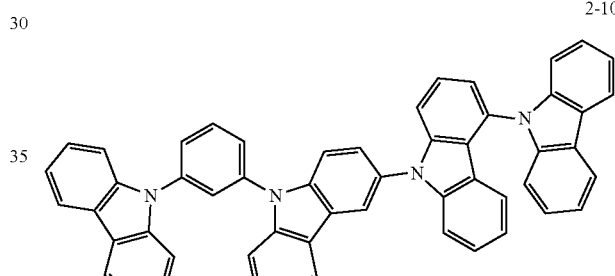
2-11
2-12
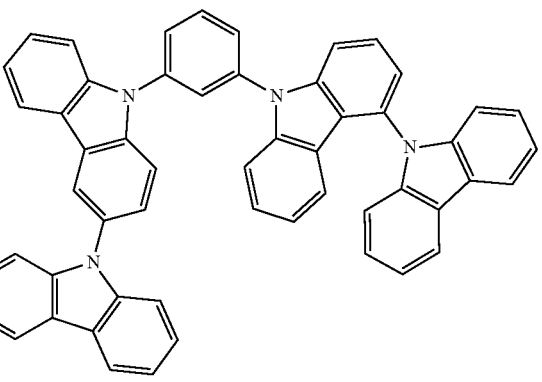

2-13
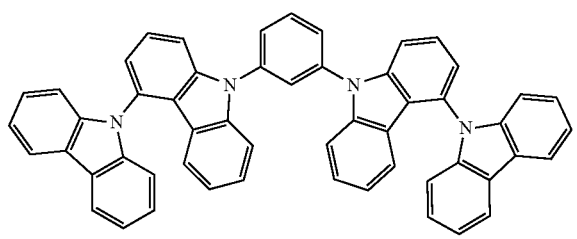
2-14
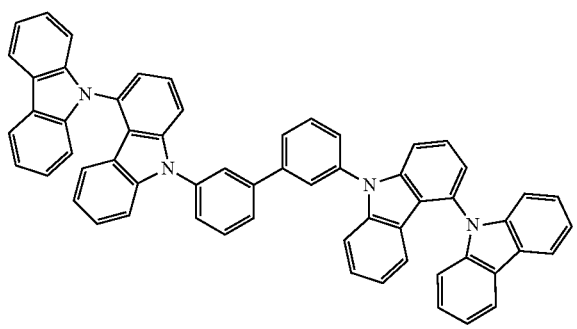
2-15
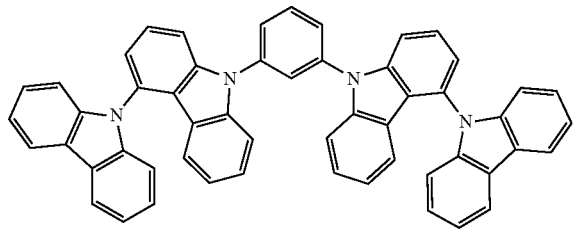
2-16
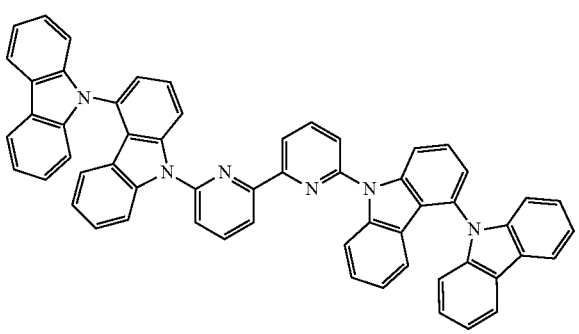
2-17
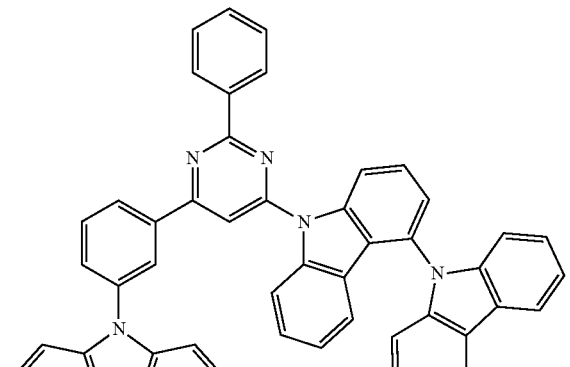
2-18
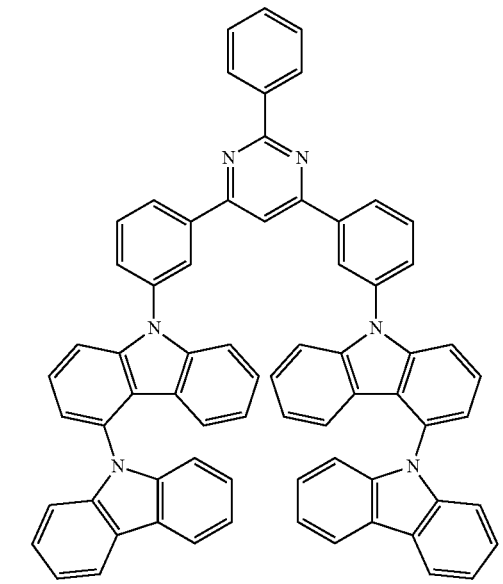
2-19
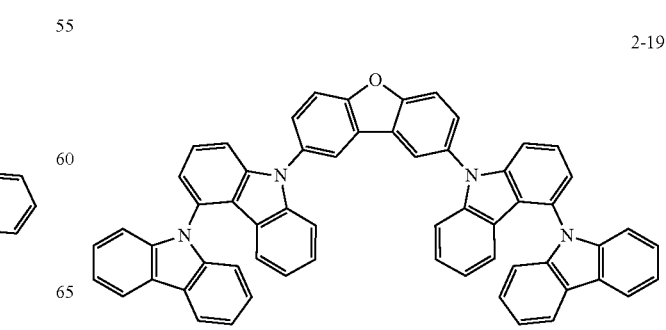

-continued
2-20
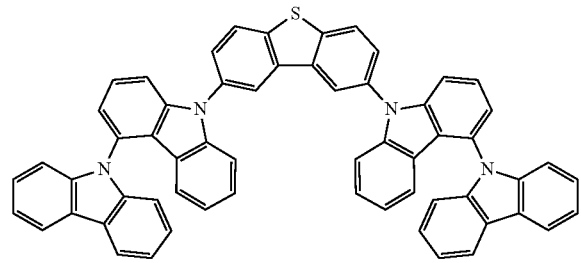
2-21
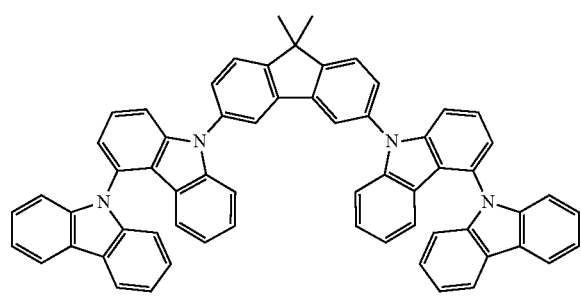
2-22
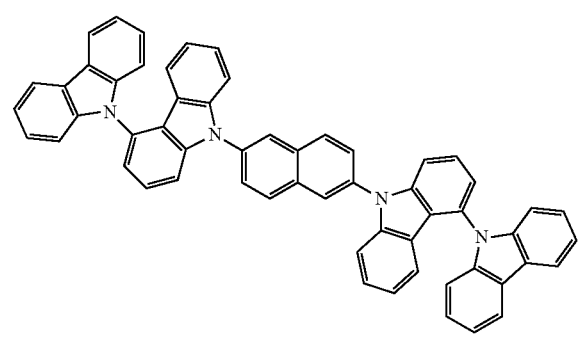
2-23
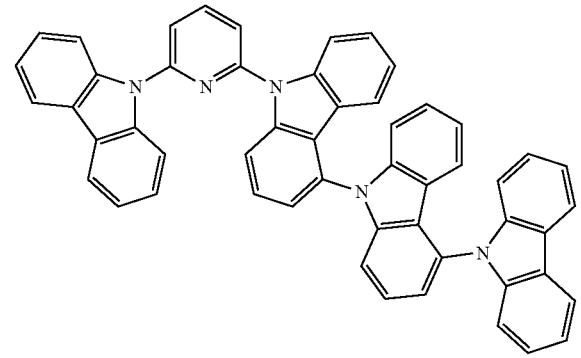
2-24
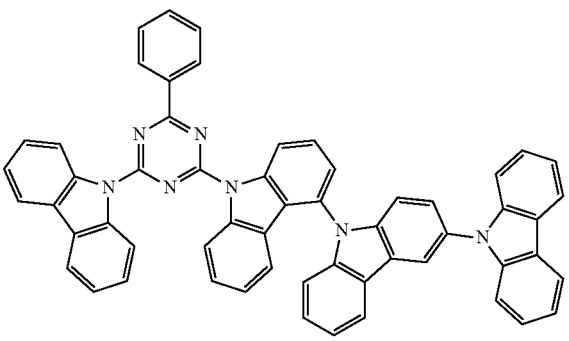
3-1
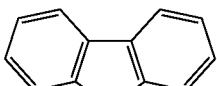
3-2
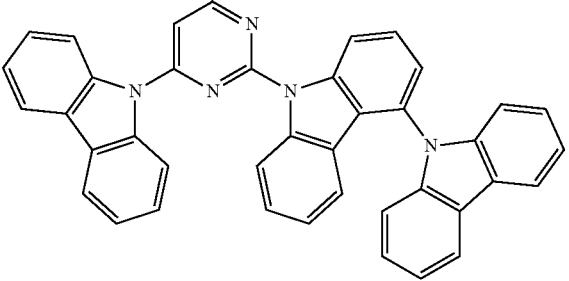

3-3

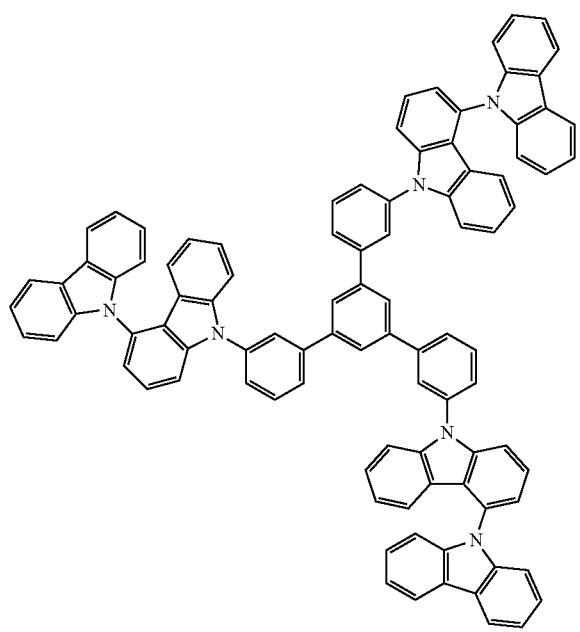

3-4

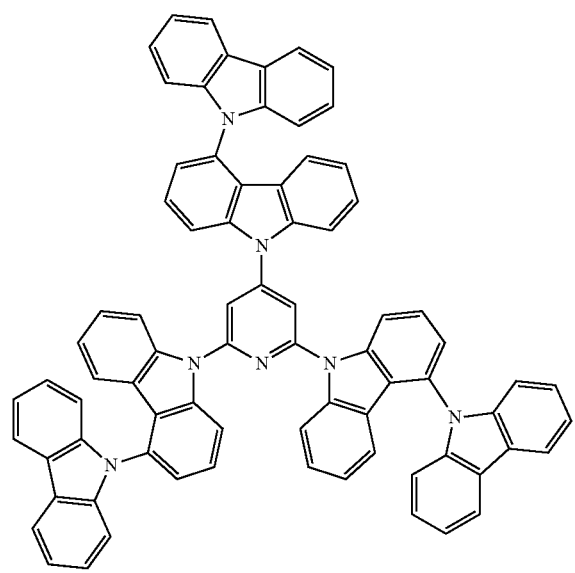

3-5

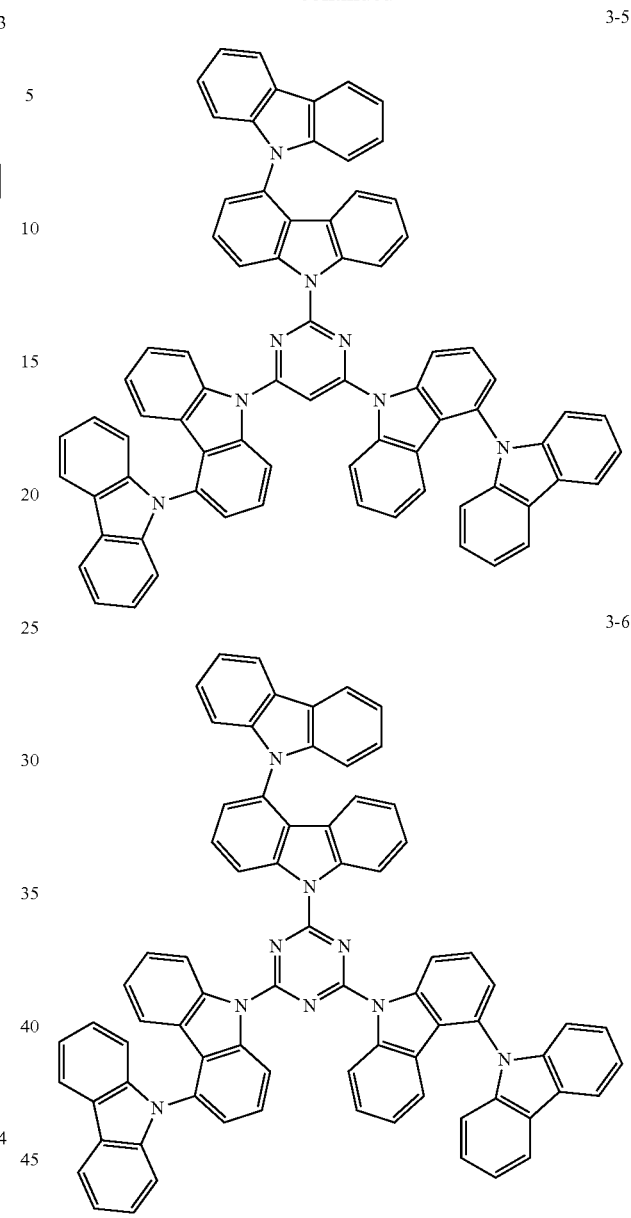

3-6

When the carbazole compound represented by the general formula (1) is incorporated in at least one of organic layers including a emitting layer, a hole-transporting layer, and an electron-blocking layer in an organic EL device formed by laminating an anode, a plurality of organic layers, and a cathode on a substrate, an excellent organic electroluminescent device is provided. A emitting layer or a hole-transporting layer is preferred as the organic layer to be incorporated. It is more preferred that the carbazole compound be incorporated as a host material in a emitting layer containing a phosphorescent light-emitting dopant.

Next, the organic EL device of the present invention is described.

The organic EL device of the present invention has organic layers including at least one emitting layer between an anode and a cathode laminated on a substrate. In addition, at least one of the organic layers including a emitting layer, a hole-transporting layer, and an electron-blocking layer contains the compound represented by the general formula (1). The compound represented by the general formula (1) is advantageously contained in the emitting layer or the hole-transporting layer, and is more advantageously contained in the emitting layer together with a phosphorescent light-emitting dopant.

Next, the structure of the organic EL device of the present invention is described with reference to the drawings. However, the structure of the organic EL device of the present invention is by no means limited to one illustrated in the drawings.

FIG. 1 is a sectional view illustrating a structural example of a general organic EL device used in the present invention. Reference numerals 1, 2, 3, 4, 5, 6, and 7 represent a substrate, an anode, a hole-injecting layer, a hole-transporting layer, a emitting layer, an electron-transporting layer, and a cathode, respectively. The organic EL device of the present invention may have an exciton-blocking layer adjacent to the emitting layer, or may have an electron-blocking layer between the emitting layer and the hole-injecting layer. The exciton-blocking layer may be inserted on any of the anode side and the cathode side of the emitting layer, and may also be inserted simultaneously on both sides. The organic EL device of the present invention has the substrate, the anode, the emitting layer, and the cathode as its essential layers. The organic EL device of the present invention preferably has a hole-injecting/transporting layer and an electron-injecting/transporting layer in addition to the essential layers, and more preferably has a hole-blocking layer between the emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure compared with FIG. 1, that is, a structure formed by laminating the layers on the substrate 1 in the order of the cathode 7, the electron-transporting layer 6, the emitting layer 5, the hole-transporting layer 4, and the anode 2. In this case as well, a layer may be added or eliminated as required.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$-ZnO), which may be used for manufacturing an amorphous, transparent conductive film. In order to produce the anode, it may be possible to form any of those electrode substances into a thin film by using a method such as vapor deposition or sputtering and form a pattern having a desired design thereon by photolithography. Alternatively, in the case of not requiring high pattern accuracy (about 100 μm or more), a pattern may be formed via a mask having a desired shape when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. Further, the sheet resistance as the anode is preferably several hundred $\Omega/\square$ or less. Further, the thickness of the resultant film is, depending on the material used, selected from usually the range of 10 to 1,000 nm, preferably the range of 10 to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode may be produced by forming any of those electrode substances into a thin film by using a method such as vapor deposition or spattering. Further, the sheet resistance as the cathode is preferably several hundred $\Omega/\square$ or less, and the thickness of the resultant film is selected from usually the range of 10 nm to 5 μm, preferably the range of 50 to 200 nm. It should be noted that, in order for luminescence produced to pass through, any one of the anode and cathode of the organic EL device is preferably transparent or semi-transparent, because the light emission luminance improves.

Further, after any of the above-mentioned metals is formed into a film having a thickness of 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Emitting Layer

The emitting layer is a phosphorescent emitting layer, and contains a phosphorescent light-emitting dopant and a host material. It is recommended to use, as a material for the phosphorescent light-emitting dopant, a material containing an organic metal complex including at least one metal selected from ruthenium, rhodium, palladium, silver, rhenium, osmium, iridium, platinum, and gold. Such organic metal complexes are known in the prior art documents and the like, and a complex is selected therefrom and may be used. The phosphorescent light-emitting dopant desirably has a local maximum emission wavelength at a wavelength of 550 nm or less.

Preferred examples of the phosphorescent light-emitting dopant include complexes such as $Ir(ppy)_3$, complexes such as $(Bt)_2Iracac$, and complexes such as (Btp)Ptacac, the complexes each having a noble metal element such as Ir as a central metal. Specific examples of those complexes are shown below, but the complexes are not limited to the compounds described below.

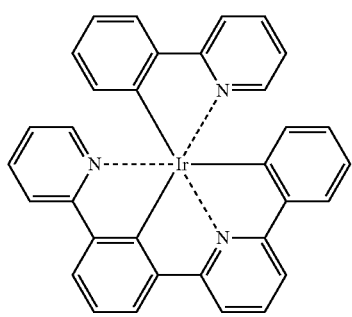
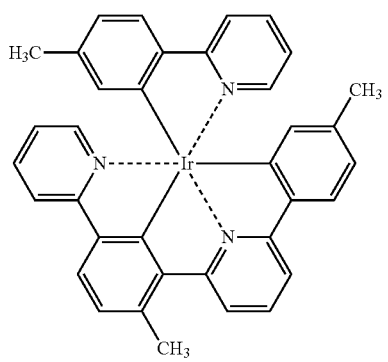
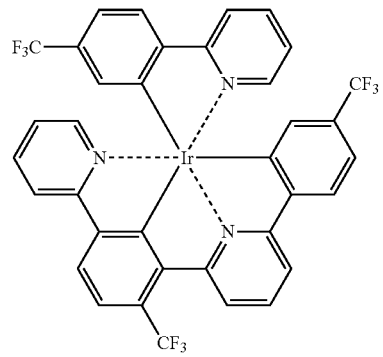
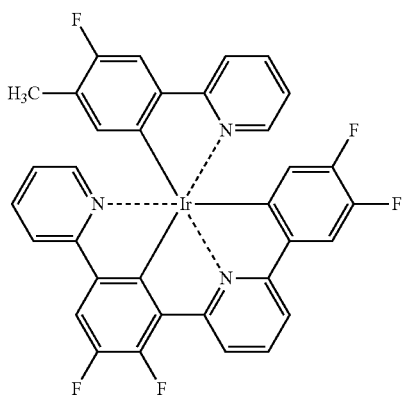
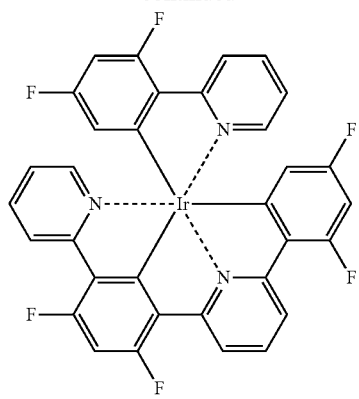
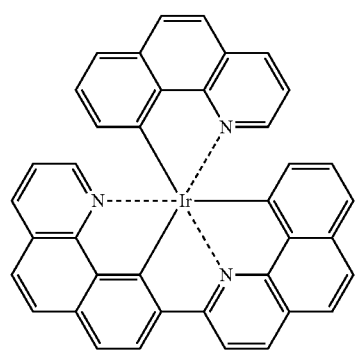
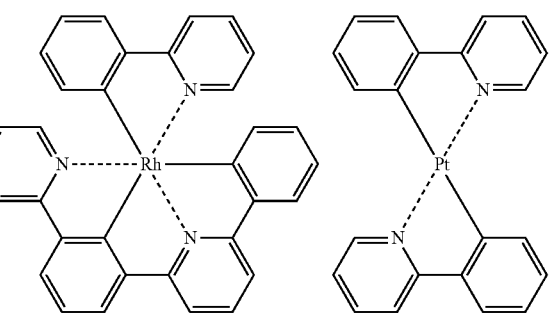
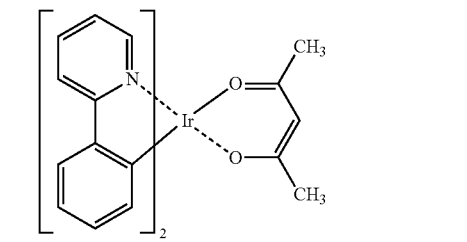

-continued
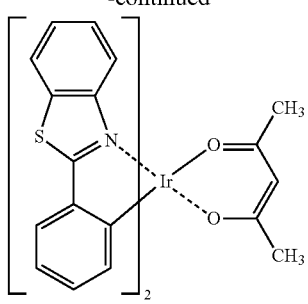
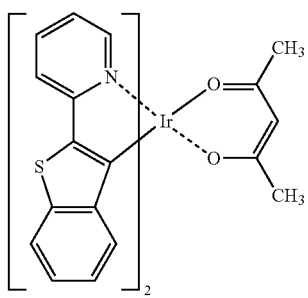
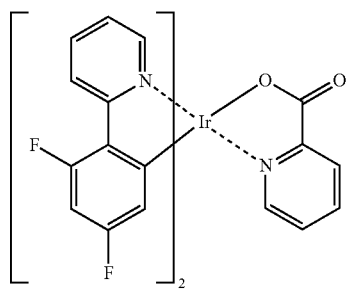
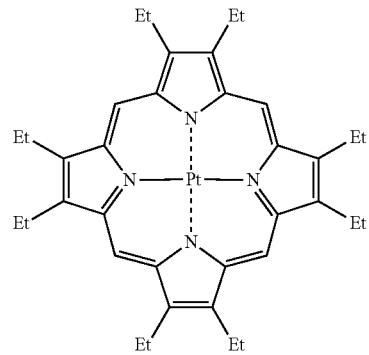
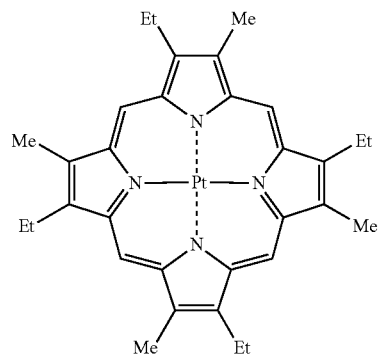
-continued
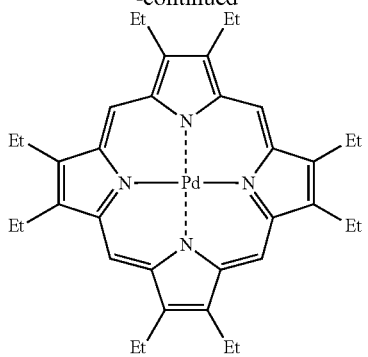
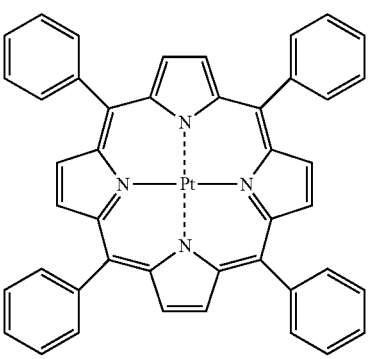
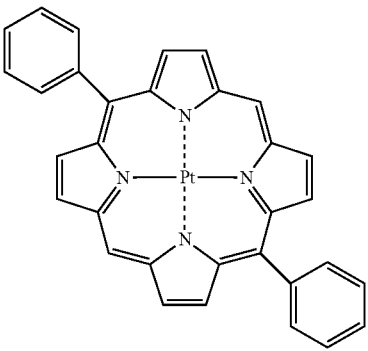
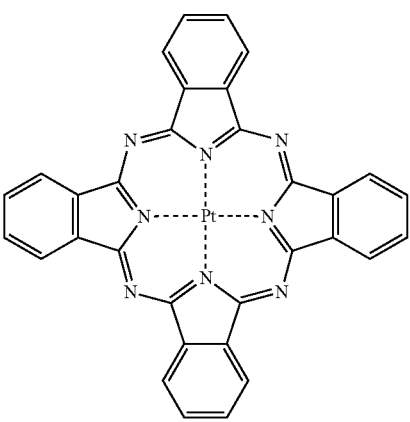

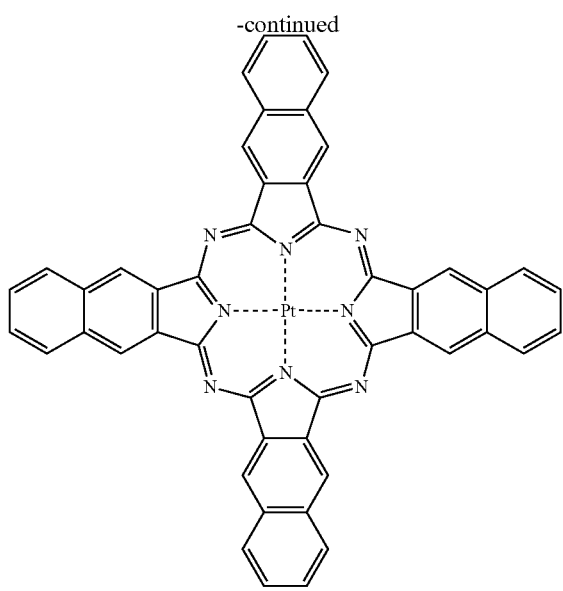

It is preferred that the content of the phosphorescent light-emitting dopant in the emitting layer be in the range of 1 to 50 wt %, more preferably 5 to 30 wt %.

It is preferred to use, as a host material in the emitting layer, the compound represented by the general formula (1). However, when the compound is used in any of the organic layers other than the emitting layer, the material to be used in the emitting layer may be any other host material other than the compound represented by the general formula (1), and the compound represented by the general formula (1) and any other host material may be used in combination. Further, a plurality of kinds of known host materials may be used in combination.

It is preferred to use, as a usable known host compound, a compound that has a hole-transporting ability or an electron-transporting ability, is capable of preventing luminescence from having a longer wavelength, and has a high glass transition temperature.

Such other host materials are known because they are mentioned in many patent literatures and the like, and hence may be chosen from those in the patent literatures and the like. Specific examples of the host material include, but not particularly limited to, an indole derivative, a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrin-based compound, an anthraquinodimethane derivative, an enthrone derivative, a diphenylquinone derivative, a thiopyrane dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly(N-vinylcarbazole) derivative, an aniline-based copolymer, a thiophene oligomer, a polythiophene derivative, a polyphenylene derivative, a polyphenylenevinylene derivative, and a polyfluorene derivative.

—Injecting Layer—

The injecting layer refers to a layer provided between an electrode and an organic layer for lowering a driving voltage and improving a light emission luminance, and includes a hole-injecting layer and an electron-injecting layer. The injecting layer may be interposed between the anode and the emitting layer or the hole-transporting layer, or may be interposed between the cathode and the emitting layer or the electron-transporting layer. The injecting layer may be provided as required.

—Hole-blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

A known material for a hole-blocking layer can foe used for the hole-blocking layer. Further, it is possible to use, as a material for the hole-blocking layer, any of the below-mentioned materials for the electron-transporting layer as required.

—Electron-blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

The compound represented by the general formula (1) is preferably used as a material for the electron-blocking layer. However, when the compound is used in any other organic layer, any of the below-mentioned materials for the hole-transporting layer can be used as required. The thickness of the electron-blocking layer is preferably 3 to 100 nm, more preferably 5 to 30 nm.

—Exciton-blocking Layer—

The exciton-blocking layer refers to a layer used for blocking excitons produced by the recombination of a hole and an electron in the emitting layer from diffusing in charge-transporting layers. Inserting this layer enables effective confinement of the excitons in the emitting layer, thereby being able to improve the luminous efficiency of the device. The exciton-blocking layer may be inserted on any of the anode side and the cathode side of the adjacent emitting layer, and may also be inserted simultaneously on both sides.

As a material for the exciton-blocking layer, there are given, for example, 1,3-dicarbazolylbenzene (mCP) and bis (2-methyl-8-quinolinolato)-4 -phenylphenolatoaluminum (III) (BAlq).

—Hole-transporting Layer—

The hole-transporting layer is formed of a hole-transporting material having a function of transporting holes, and a single hole-transporting layer or a plurality of hole-transporting layers may be provided.

The hole-transporting material has any one of hole-injecting property, hole-transporting property, and electron-blocking property, and any of an organic compound and an inorganic compound may be used. It is preferred to use the compound represented by the general formula (1) as the hole-transporting material. However, when the compound is used in any other organic layer, any compound selected from conventionally known compounds may be used. Examples of the known hole-transporting material that may be used include a triazole derivative, an oxadiazole derivative, an imidazole derivative, a polyarylalkane derivative, a pyrazolone derivative and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular weight oligomer, in particular, a thiophene oligomer. However, a porphyrin compound, an aromatic tertiary amine compound, or a styrylamine compound is preferably used, and an aromatic tertiary amine compound is more preferably used.

—Electron-transporting Layer—

The electron-transporting layer is formed of a material having a function of transporting electrons, and a single electron-transporting layer or a plurality of electron-transporting layers may be provided.

An electron-transporting material (which also serves as a hole-blocking material in some cases) has only to have a function of transferring electrons injected from the cathode into the emitting layer. For the electron-transporting layer, any compound selected from conventionally known compounds may be used. Examples thereof include a nitro-substituted fluorene derivative, a diphenylquinone derivative, a thiopyran dioxide derivative, carbodiimide, a fluorenylidenemethane derivative, anthraquinodimethane and an anthrone derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative that has a quinoxaline ring known as an electron withdrawing group. Further, it is also possible to use a polymer material in which any of those materials is introduced in a polymer chain or is used as a polymer main chain.

EXAMPLES

Hereinafter, the present invention is described in more detail with reference to examples. It should be appreciated that the present invention is not limited to these examples and may be carried out in various forms as long as the various forms do not deviate from the gist of the present invention.

The routes described below were used to synthesize the compound represented by the general formula (1) used in the present invention. It should be noted that the number of each compound corresponds to the number given to each chemical formula described above.

Synthesis Example 1

Synthesis of Compound 1-3

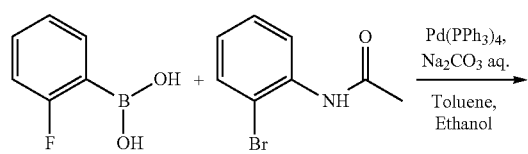

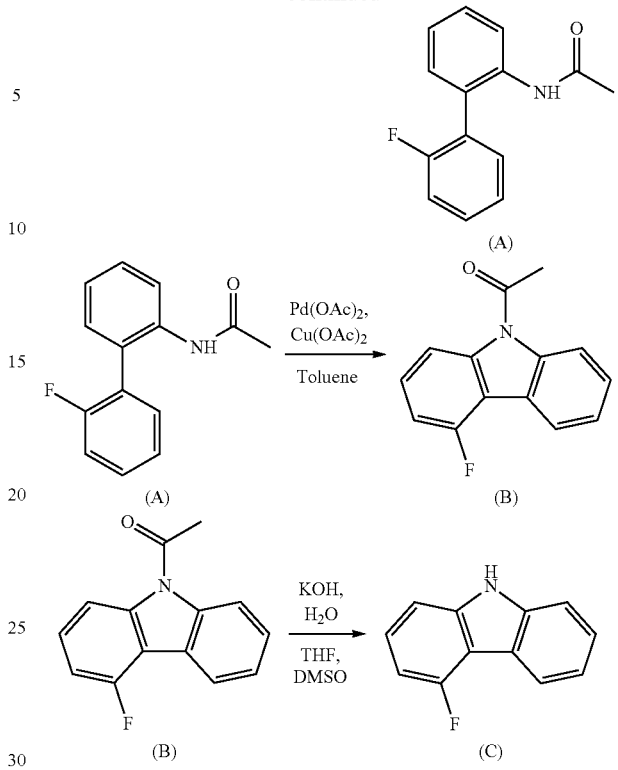

Under a nitrogen atmosphere, 60.0 g (0.43 mol) of o-fluorophenylboric acid, 40.0 g (0.29 mol) of 2-bromoacetanilide, 13.2 g (0.011 mol) of tetrakis(triphenylphosphine)palladium (0), a solution of 109 g of sodium carbonate in water (500 ml), 1,000 ml of toluene, and 400 ml of ethanol were loaded, and then the mixture was stirred overnight while being heated at 90° C. After the reaction solution had been cooled to room temperature, 500 ml of toluene and distilled water (500 ml) were added to the solution while the solution was stirred. The organic layer was washed with distilled water (3×500 ml). After the organic layer had been dried with anhydrous magnesium sulfate, magnesium sulfate was separated, by filtration and then the solvent was distilled off under reduced pressure. The resultant residue was purified by silica gel column chromatography to provide 32.1 g (0.14 mol, 49% yield) of an intermediate A as a white solid.

Under a nitrogen atmosphere, 32.0 g (0.14 mol) of an intermediate A, 16.0 g (0,070 mol) of palladium(II) acetate, 25.2 g (0.14 mol) of copper (II) acetate, and 1,390 ml of toluene were loaded, and then the mixture was stirred overnight while being heated at 110° C. After the reaction solution had been cooled to room temperature, 500 ml of toluene and distilled water (500 ml) were added to the solution while the solution was stirred. The organic layer was washed with distilled water (3×500 ml). After the organic layer had been dried with anhydrous magnesium sulfate, magnesium sulfate was separated by filtration and then the solvent was distilled off under reduced pressure. The resultant residue was purified by silica gel column chromatography to provide 12.0 g (0.065 mol, 47% yield) of an intermediate B as a white solid.

Under a nitrogen atmosphere, 8.2 g (0.036 mol) of the intermediate B, 60 ml of tetrahydrofuran (THF), 30 ml of dimethyl sulfoxide, 10.0 g (0.18 mol) of potassium hydroxide, and distilled water (3 ml) were loaded, and then the mixture was stirred for 30 minutes while being heated at 80°

C. After the reaction solution had been cooled to room temperature, 300 ml of ethyl acetate and distilled water (100 ml) were added to the solution while the solution was stirred. The organic layer was washed with distilled water (3×200 ml). After the organic layer had been dried with anhydrous magnesium sulfate, magnesium sulfate was separated by filtration and then the solvent was distilled off under reduced pressure to provide 6.4 g (0.034 mol, 95% yield) of an intermediate C as a yellow solid.

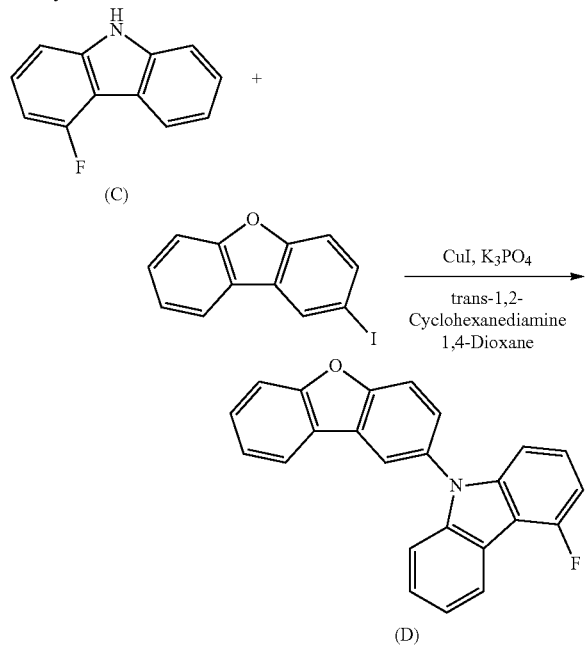

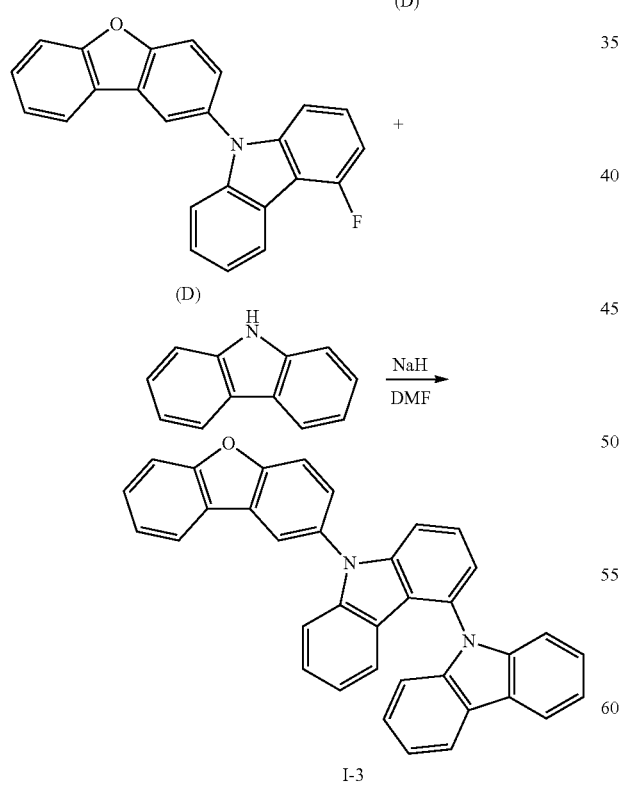

Under a nitrogen atmosphere, 6.4 g (0.034 mol) of the intermediate C, 21.5 g (0.073 mol) of 2-iododibenzofuran, 36.2 g (0.19 mol) of copper iodide, 40.3 g (0.19 mol) of tripotassium phosphate, 23.1 ml (0.19 mol) of trans-1,2-cyclohexanediamine, and 162 ml of 1,4-dioxane were loaded, and then the mixture was stirred overnight at 120° C. After the reaction solution had been cooled to room temperature, the precipitated crystal was collected by filtration and then the solvent was distilled off under reduced pressure. The resultant residue was purified by silica gel column chromatography to provide 7.0 g (0.020 mol, 58% yield) of an intermediate D as a white solid.

Under a nitrogen atmosphere, 1.9 g (0.048 mol) of sodium hydride (62.0% product) and 12 ml of dehydrated N,N-dimethylformamide (DMF) were loaded, and then the mixture was stirred at room temperature for 0.5 hour. A solution of 6.7 g (0.040 mol) of carbazole in DMF (25 ml) was added to the resultant suspension and then the mixture was stirred at room temperature for 30 minutes. 7.0 g (0.020 mol) of the intermediate D were added to the resultant suspension and then the mixture was stirred at 130° C for 3 days. After the reaction solution had been cooled to room temperature, distilled water (500 ml) was added to the solution while the solution was stirred, and then the precipitated solid was collected by filtration. The resultant solid was subjected to silica gel column chromatography and crystallization purification to provide 2.2 g (0.0044 mol, 22.2% yield) of a compound 1-3 as a white solid.

Figure 2:
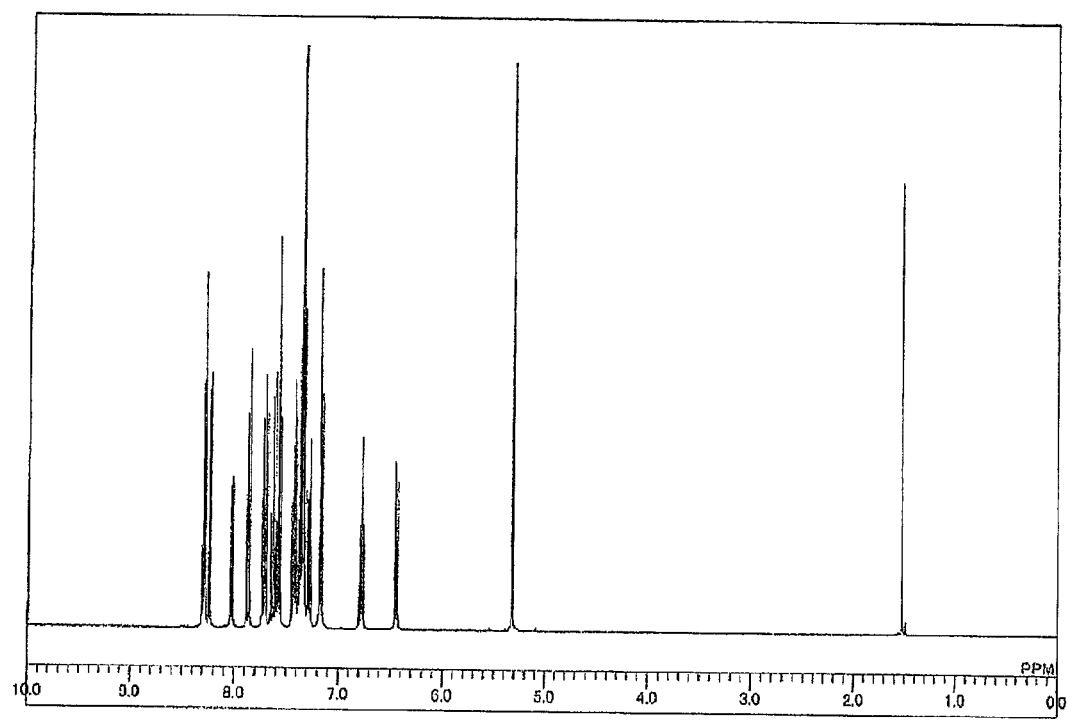
[FIG. 2] $^1$H-NMR chart of a compound 1-3.

The APCI-TOFMS of the compound showed an [M]+ ion peak at an m/z of 498. FIG. 2 shows the results of its $^1$H-NMR measurement (measurement solvent: $CD_2Cl_2$).

Synthesis Example 2

Synthesis of Compound 1-15

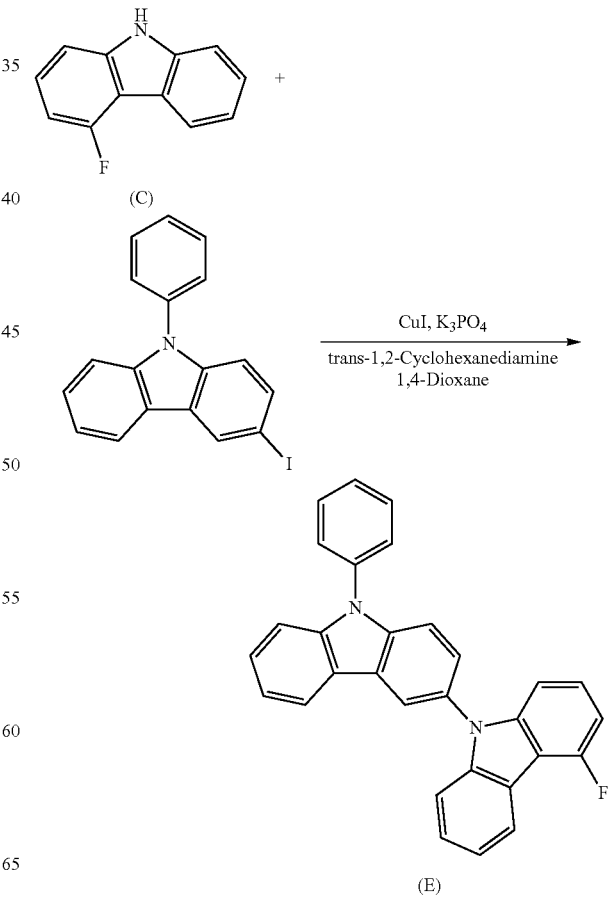

-continued

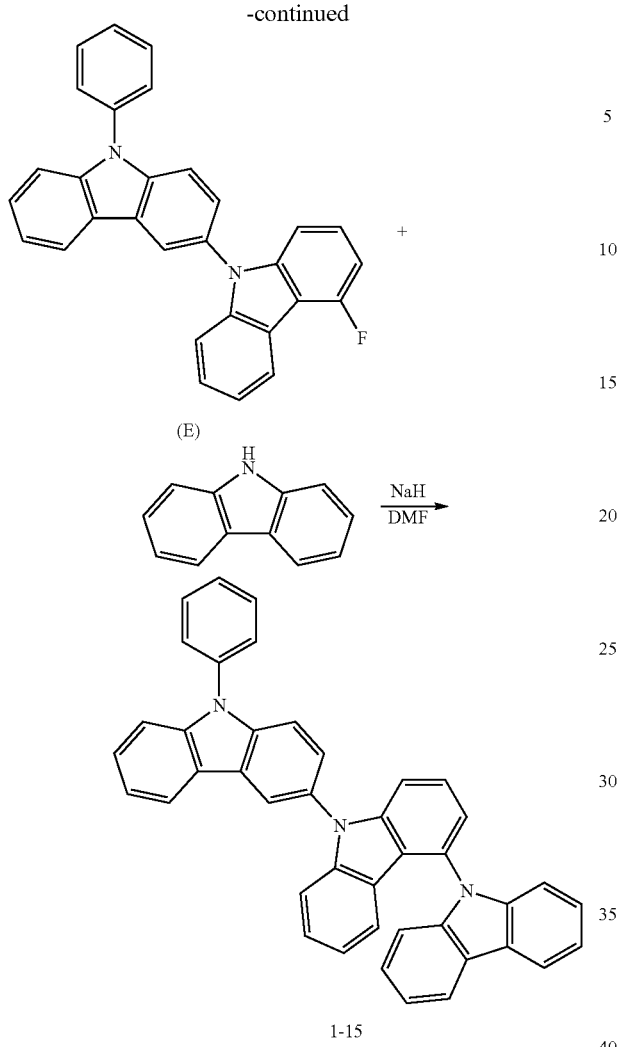

(E)

1-15

Under a nitrogen atmosphere, 7.6 g (0.041 mol) of the intermediate C, 10.0 g (0.027 mol) of 3-iodo-9-phenylcarbazole, 20.9 g (0.11 mol) of copper iodide, 23.3 g (0.11 mol) of tripotassium phosphate, 13.2 ml (0.11 mol) of trans-1,2-cyclohexanediamine, and 135 ml of 1,4-dioxane were loaded, and then the mixture was stirred for 4 hours at 120° C. After the reaction solution had been cooled to room temperature, the precipitated crystal was collected by filtration and then the solvent was distilled off under reduced pressure. The resultant residue was purified by silica gel column chromatography to provide 9.8 g (0.02 3 mol, 87% yield) of an intermediate E as a white solid.

Under a nitrogen atmosphere, 2.2 g (0.056 mol) of sodium hydride (62.0% product) and 14 ml of DMF were loaded, and then the mixture was stirred at room temperature for 0.5 hour. A solution of 7.8 g (0.047 mol) of carbazole in DMF (33 ml) was added to the resultant suspension and then the mixture was stirred at room temperature for 30 minutes. 9.8 g (0.02 3 mol) of the intermediate E were added to the resultant suspension and then the mixture was stirred at 130° C for 3 days. After the reaction solution had been cooled to room temperature, distilled water (1,000 ml) was added to the solution while the solution was stirred, and then the precipitated yellow solid was collected by filtration. The resultant yellow solid was subjected to silica gel column chromatography to provide 2.4 g (0.0042 mol, 18% yield) of a compound 1-15 as a white solid.

Figure 3:
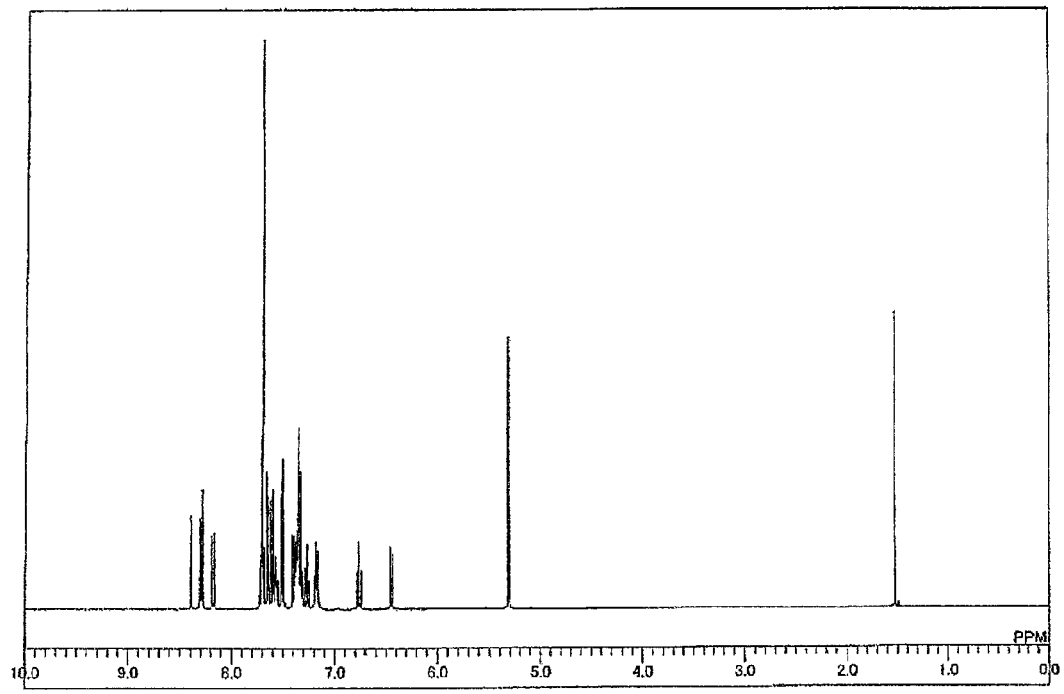
[FIG. 3] $^1$H-NMR chart of a compound 1-15.

The APCI-TOFMS of the compound showed an [M-H]$^+$ ion peak at an m/z of 574. FIG. 3 shows the results of its $^1$H-NMR measurement (measurement solvent: $CD_2Cl_2$).

Synthesis Example 3

Synthesis of Compound 1-21

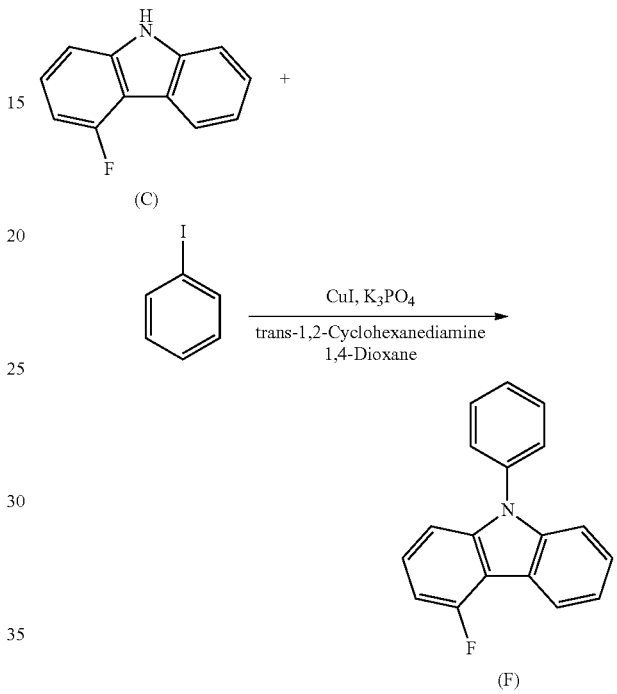

(F)

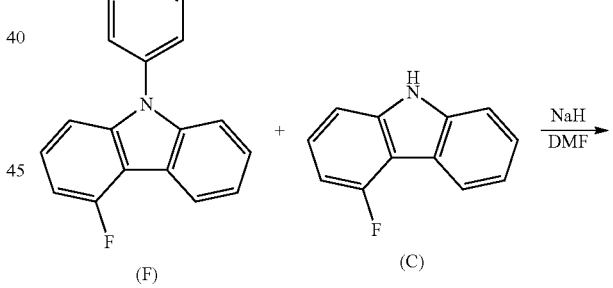

(F)                (C)

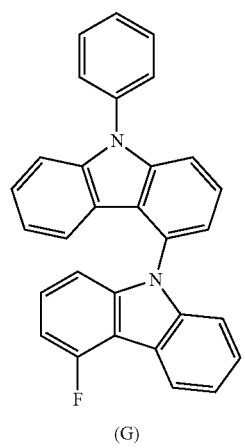

(G)

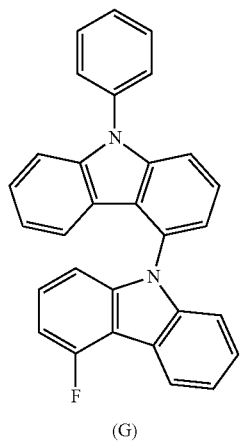

(G)

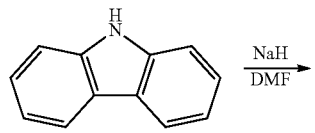

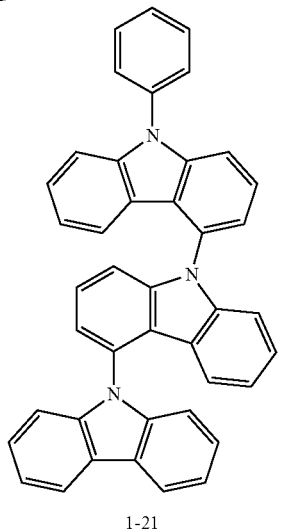

1-21

Under a nitrogen atmosphere, 5.1 g (28.0 mmol) of the intermediate C, 5.6 g (27.4 mmol) of iodobenzene, 0.17 g (0.89 mmol) of copper iodide, 29.3 g (138 mmol) of tripotassium phosphate, 1.05 g (9.2 mmol) of trans-1,2-cyclohexanediamine, and 150 ml of 1,4-dioxane were loaded, and then the mixture was stirred for 2 hours at 115° C. After the reaction solution had been cooled to room temperature, the precipitated crystal was collected by filtration and then the solvent was distilled off under reduced pressure. The resultant residue was purified by silica gel column chromatography to provide 5.6 g (3.8 mmol, 14% yield) of an intermediate F as a white solid.

Under a nitrogen atmosphere, 1.9 g (50.7 mmol) of sodium hydride (63.0% product) and 50 ml of DMF were loaded, and then the mixture was stirred at room temperature for 0.5 hour. A solution of 9.4 g (50.7 mmol) of the intermediate C in DMF (35 ml) was added to the resultant suspension and then the mixture was stirred at room temperature for 20 minutes. A solution of 13.2 g (50.7 mmol) of the intermediate F in DMF (35 ml) was added to the resultant suspension and then the mixture was stirred overnight at 115° C. After the reaction solution had been cooled to room temperature, distilled water (1,000 ml) was added to the solution while the solution was stirred, and then the precipitated yellow solid was collected by filtration. The resultant yellow solid was subjected to silica gel column chromatography to provide 3.8 g (8.9 mmol, 18% yield) of an intermediate G as a white solid.

Under a nitrogen atmosphere, 0.62 g (16.4 mmol) of sodium hydride (63.0% product) and 50 ml of DMF were loaded, and then the mixture was stirred at room temperature for 0.5 hour. A solution of 2.7 g (16.4 mmol) of carbazole in DMF (25 ml) was added to the resultant suspension and then the mixture was stirred at room temperature for 30 minutes. A solution of 3.5 g (8.2 mmol) of the intermediate G in DMF (25 ml) was added to the resultant suspension and then the mixture was stirred overnight at 115° C. After the reaction solution had been cooled to room temperature, distilled water (150 ml) was added to the solution while the solution was stirred, and then the precipitated yellow solid was collected by filtration. The resultant yellow solid was subjected to silica gel column chromatography to provide 1.5 g (2.6 mmol, 32% yield) of a compound 1-21 as a white solid.

Figure 4:
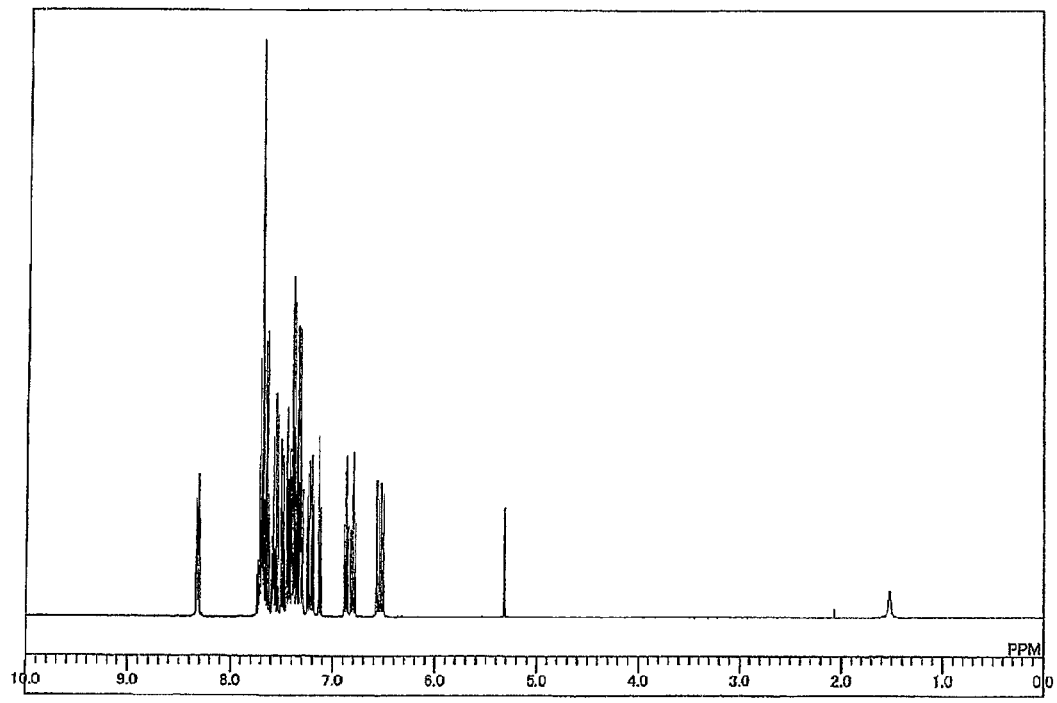
[FIG. 4] $^1$H-NMR chart of a compound 1-21.

The APCI-TOFMS of the compound showed an [M-H]+ ion peak at an m/z of 574. FIG. 4 shows the results of its $^1$H-NMR measurement (measurement solvent: $CD_2Cl_2$).

Synthesis Example 4

Synthesis of Compound 1-2

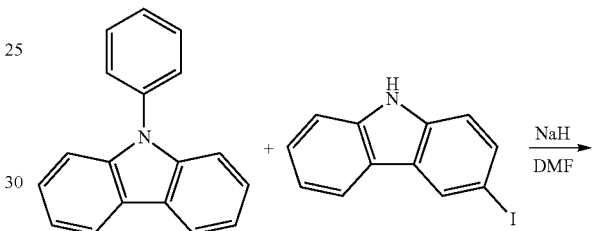

(F)

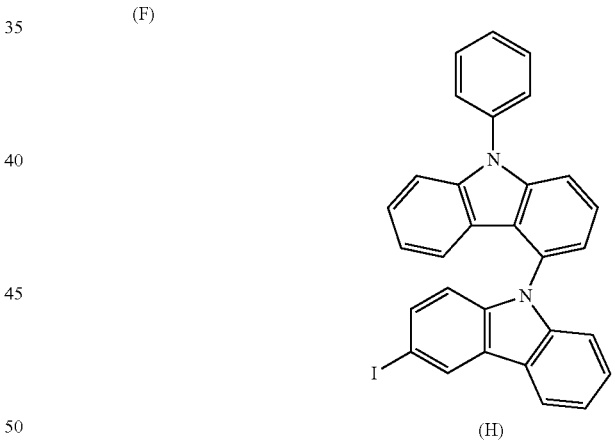

(H)

(H)

-continued

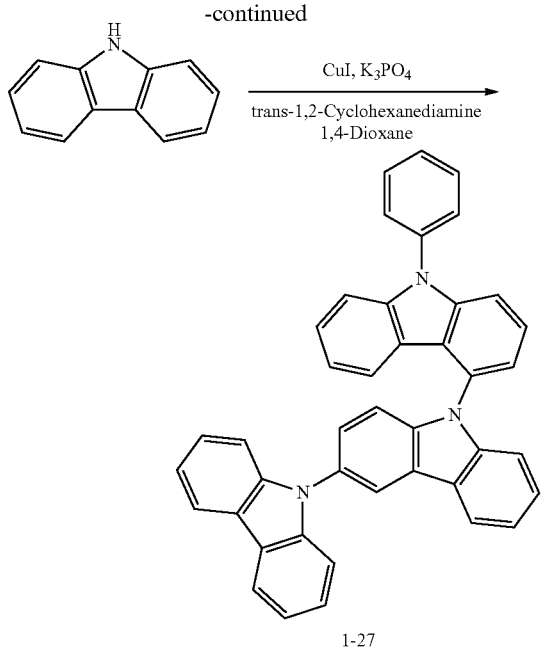

1-27

Under a nitrogen atmosphere, 2.73 g (0.0706 mol) of sodium hydride (63.0% product) and 50 ml of DMF were loaded, and then the mixture was stirred at room temperature for 0.5 hour. A solution of 18.8 g (0.0642 mol) of 3-iodocarbazole in DMF (30 ml) was added to the resultant suspension and then the mixture was stirred at room temperature for 20 minutes. A solution of 8.4 g (0.0321 mol) of the intermediate F in DMF (30 ml) was added to the resultant suspension and then the mixture was stirred at 120° C. for 69 hours. After the reaction solution had been cooled to room temperature, distilled water (300 ml) was added to the solution while the solution was stirred, and then the precipitated yellow solid was collected by filtration. The resultant yellow solid was subjected to silica gel column chromatography to provide 14.9 g (0.028 mol, 87% yield) of an intermediate H as a white solid.

Figure 5:
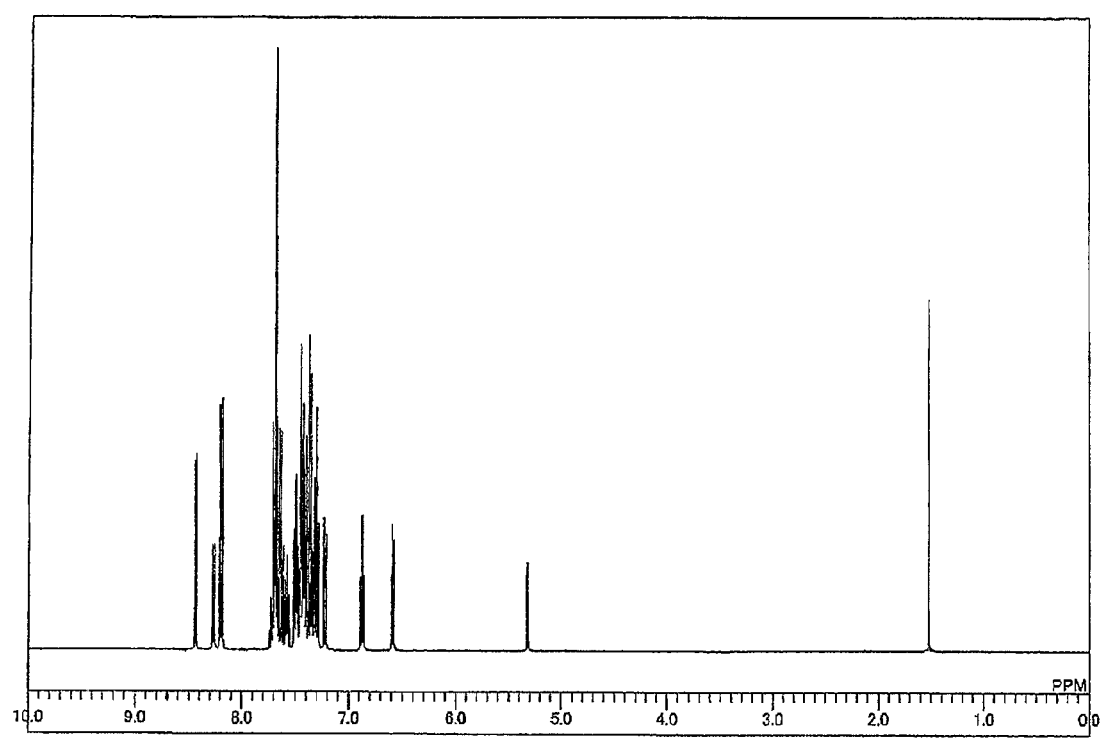
[FIG. 5] $^1$H-NMR chart of a compound 1-27.

Under a nitrogen atmosphere, 14.0 g (0.0262 mol) of the intermediate H, 8.7 g (0.0524 mol) of carbazole, 0.99 g (0.0052 mol) of copper iodide, 22.2 g (0.104 mol) of tripotassium phosphate, 5.98 g (0.0524 mol) of trans-1,2-cyclohexanediamine, and 400 ml of 1,4-dioxane were loaded, and then the mixture was stirred at 110° C. for 8 hours. After the reaction solution had been cooled to room temperature, the precipitated crystal was collected by filtration and then the solvent was distilled off under reduced pressure. The resultant residue was purified by silica gel column chromatography to provide 12.4 g (0.0217 mol, 83% yield) of a compound 1-27 as a white solid. The APCI-TOFMS of the compound showed an [M+H]$^+$ ion peak at an m/z of 574. FIG. 5 shows the results of its $^1$H-NMR measurement (measurement solvent: CD$_2$Cl$_2$).

In addition, compounds 1-8, 1-11, 1-17, 1-25, 1-28, 1-30, 2-13, 2-22, 2-23, and 3-6 were synthesized in conformity with the synthetic method described in Synthesis Examples and the description, and were used for the production of the organic EL device.

Example 1

In the organic EL device illustrated in FIG. 1, a device in which an electron-injecting layer was added between the electron-transporting layer and the cathode was produced. Each thin film was laminated by a vacuum deposition method at a degree of vacuum of 2.0×10$^{-5}$ Pa on a glass substrate on which an anode formed of indium tin oxide (ITO) having a thickness of 110 nm had been formed. First, copper phthalocyanine (CuPC) was formed into a layer having a thickness of 25 nm to serve as a hole-injecting layer on the ITO. Next, N,N-di(naphthalene-1-yl)-N,N-diphenyl-benzidene (NPB) was formed into a layer having a thickness of 90 nm to serve as a hole-transporting layer. Next, the compound (1-3) as a host material for a emitting layer and an iridium complex (iridium(III) bis [(4,6-difluorophenyl)-pyridinato-N,C2']picolinate) (FIrpic) as a blue phosphorescent light-emitting material as a dopant were co-deposited from different deposition sources onto the hole-transporting layer to form a emitting layer having a thickness of 30 nm. The concentration of FIrpic was 10.0 wt %. Next, Alq3 was formed into a layer having a thickness of 30 nm to serve as an electron-transporting layer. Further, lithium fluoride (LiF) was formed into a layer having a thickness of 1.0 nm to serve as an electron-injecting layer on the electron-transporting layer. Finally, aluminum (Al) was formed into a layer having a thickness of 70 nm to serve as an electrode on the electron-injecting layer. Thus, an organic EL device was produced.

Examples 2 to 11

Organic EL devices were each produced in the same manner as in Example 1 except that the compound 1-8, the compound 1-11, the compound 1-15, the compound 1-17, the compound 1-21, the compound 1-27, the compound 1-30, the compound 2-13, the compound 2-23, or the compound 3-6 was used as the host material for the emitting layer.

Comparative Examples 1 and 2

Organic EL devices were each produced in the same manner as in Example 1 except that mCP or the following compound H-1 was used as the host material for the emitting layer.

H-1

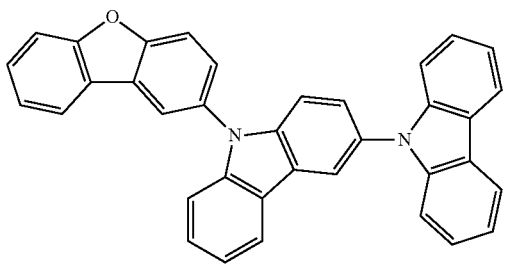

An external power source was connected to each of the organic EL devices obtained in Examples and Comparative Examples to apply a DC voltage to the devices. As a result, the devices were observed to have such light-emitting characteristics (initial characteristics) as shown in Table 1. It should be noted that it was found that the local maximum wavelength of the emission spectrum of each of the devices was 475 nm and hence light emission from FIrpic was obtained.

In Table 1, the column "compound" shows the compound used as the host material, and the columns "luminance," "voltage," and "luminous efficiency" show values at 2.5 mA/cm$^2$.

TABLE 1

| | compound | luminance (cd/m$^2$) | voltage (V) | luminous efficiency (lm/W) |
|---|---|---|---|---|
| | | initial characteristics | | |
| Example 1 | 1-3 | 180 | 8.8 | 2.6 |
| 2 | 1-15 | 191 | 8.7 | 2.8 |
| 3 | 1-17 | 195 | 8.8 | 2.8 |
| 4 | 1-30 | 189 | 8.6 | 2.8 |
| 5 | 2-23 | 199 | 9.0 | 2.8 |
| 6 | 3-6 | 179 | 8.0 | 2.8 |
| 7 | 1-8 | 211 | 8.1 | 3.3 |
| 8 | 1-11 | 210 | 8.2 | 3.2 |
| 9 | 1-21 | 190 | 8.7 | 2.7 |
| 10 | 1-27 | 193 | 8.7 | 2.8 |
| 11 | 2-13 | 215 | 8.4 | 3.2 |
| Comparative Example 1 | mCP | 140 | 8.7 | 2.0 |
| 2 | H-1 | 134 | 8.1 | 2.1 |

Table 1 shows that in the case where the compound represented by the general formula (1) is used in the emitting layer in each of Examples 1 to 11, a high luminous efficiency characteristic is obtained as compared with the case where mCP generally known as a phosphorescent host material or the H-1 different from the compound in substitution position of carbazole is used.

Example 12

Each thin film was laminated by a vacuum deposition method at a degree of vacuum of 2.0×10$^{-5}$ Pa on a glass substrate on which an anode formed of an ITO substrate having a thickness of 110 nm had been formed. First, CuPC was formed into a layer having a thickness of 25 nm to serve as a hole-injecting layer on the ITO. Next, NPB was formed into a layer having a thickness of 40 nm to serve as a hole-transporting layer. Next, the compound 1-3 as a host material and Ir(ppy)$_3$ as a dopant were co-deposited from different deposition sources onto the hole-transporting layer to form a emitting layer having a thickness of 40 nm. At this time, the concentration of Ir(ppy)$_3$ was 10 wt %. Next, Alq3 was formed into a layer having a thickness of 20 nm to serve as an electron-transporting layer. Further, LiF was formed into a layer having a thickness of 1 nm to serve as an electron-injecting layer on the electron-transporting layer. Finally, Al was formed into a layer having a thickness of 70 nm to serve as an electrode on the electron-injecting layer. Thus, an organic EL device was produced.

Examples 13 to 25

Organic EL devices were each produced in the same manner as in Example 12 except that the compound 1-8, the compound 1-11, the compound 1-15, the compound 1-17, the compound 1-21, the compound 1-25, the compound 1-27, the compound 1-28, the compound 1-30, the compound 2-13, the compound 2-22, the compound 2-23, or the compound 3-6 was used as the host material for the emitting layer, Comparative Examples 3 and 4

Organic EL devices were each produced in the same manner as in Example 12 except that CBP or H-1 was used as the host material for the emitting layer.

An external power source was connected to each of the organic EL devices obtained in Examples 12 to 25 and Comparative Examples 3 and 4 to apply a DC voltage to the devices. As a result, the devices were observed to have such light-emitting characteristics as shown in Table 2. It should be noted that it was found that the local maximum wavelength of the emission spectrum of each of the devices was 530 nm and hence light emission from Ir(ppy)$_3$ was obtained.

In Table 2, the column "compound" shows the compound used as a host material, and the columns "luminance," "voltage," and "luminous efficiency" show values at the time of driving at 20 mA/cm$^2$. In addition, the column "half lifetime" shows a value obtained by evaluating the half-life in the case of driving at a constant current of 20 mA/cm$^2$ and converting the result into a value in the case of an initial luminance of 1,000 cd/m$^2$.

TABLE 2

| | compound | luminance (cd/m$^2$) | voltage (V) | luminous efficiency (lm/W) | half lifetime (hours) |
|---|---|---|---|---|---|
| | | initial characteristics | | | |
| Example 12 | 1-3 | 2220 | 9.1 | 3.8 | 2000 |
| 13 | 1-15 | 1940 | 9.2 | 3.3 | 2880 |
| 14 | 1-17 | 2300 | 9.1 | 4.0 | 2980 |
| 15 | 1-25 | 1770 | 9.0 | 3.1 | 2230 |
| 16 | 1-28 | 2400 | 9.0 | 4.2 | 3000 |
| 17 | 1-30 | 2330 | 9.1 | 4.0 | 2990 |
| 18 | 2-23 | 2300 | 8.9 | 4.1 | 2650 |
| 19 | 3-6 | 1820 | 8.2 | 3.5 | 2990 |
| 20 | 1-8 | 2200 | 8.2 | 4.2 | 3600 |
| 21 | 1-11 | 2100 | 8.1 | 4.0 | 3550 |
| 22 | 1-21 | 1950 | 9.0 | 3.4 | 2900 |
| 23 | 1-27 | 1990 | 9.0 | 3.4 | 2950 |
| 24 | 2-13 | 2100 | 8.4 | 3.9 | 3100 |
| 25 | 2-22 | 1800 | 8.9 | 3.2 | 3030 |
| Comparative Example 3 | CBP | 1120 | 8.7 | 2.0 | 1120 |
| 4 | H-1 | 1320 | 9.3 | 2.2 | 1220 |

Table 2 shows that Examples 12 to 25 each using the compound represented by the general formula (1) in the emitting layer each have a higher luminous efficiency characteristic than that in the case where CBP generally known as a phosphorescent host material or the H-1 different from the compound in substitution position of carbazole is used. Further, Table 2 shows that the examples each have a good operating lifetime characteristic and high stability.

It is assumed from the foregoing results that the carbazole compound represented by the general formula (1) has a 4-(9-carbazolyl)carbazole structure, and hence can control the expansion of a molecular orbital and exerts the following effects: the optimization of a charge balance and an improvement in stability against both charges. In addition, it is apparent that a high-efficiency organic EL phosphorescent device is realized by using the compound in its emitting layer.

INDUSTRIAL APPLICABILITY

The carbazole compound used in the present invention has a 4-(9-carbazolyl)carbazole structure. Such compound formed only of a 3-(9-carbazolyl) carbazole structure as described in Patent Literature 5 has been known as a compound in which a plurality of carbazoles are linked to each other. The compound of the present invention has a 4-(9-carbazolyl) carbazole structure and hence shows higher hole-transporting property than that in the case where carbazoles are linked to each other only at any other position. In addition, the substitution of a linking group with a specific aromatic group may be able to improve its electron-transporting property while securing the high hole-transporting property.

Therefore, it is assumed that when the carbazole compound used in the present invention is used as a host material, the transporting properties for both charges improve and hence the probability of their recombination in the emitting layer increases. It is assumed that the organic EL device of the present invention achieves high luminous efficiency by virtue of the foregoing effects, and hence an organic EL device Laving a long operating lifetime and high durability can be realized.

The organic EL device according to the present invention has light emission characteristics, operating lifetime, and durability at practically satisfactory levels. Thus, the organic EL device has a large technical value in applications to flat panel displays (display devices for portable phones, in-vehicle display devices, display devices for OA computers, televisions, and the like), light sources exerting characteristics of planar light emitters (light sources in lighting equipment and copiers and backlight sources in liquid crystal displays and instruments), sign boards, sign lamps, and the like.

The invention claimed is:

1. An organic electroluminescent device, comprising an anode, a plurality of organic layers, and a cathode laminated on a substrate, wherein the organic electroluminescent device contains a carbazole compound represented by the general formula (1) in at least one layer selected from the group consisting of a emitting layer, a hole-transporting layer, and an electron-blocking layer:

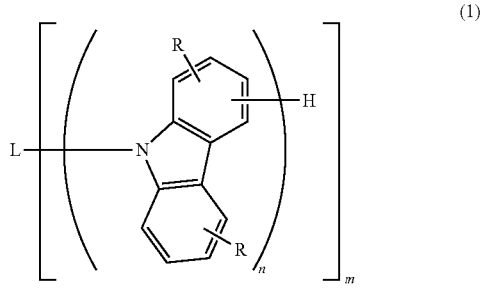

(1)

where L represents an m-valent aromatic hydrocarbon group having 6 to 30 carbon atoms in total or aromatic heterocyclic group having 3 to 30 carbon atoms in total, but does not represent a carbazole ring-containing group, R's each independently represent hydrogen, an alkyl group having 1to 10carbon atoms, or a cycloalkyl group having, 3 to 11 carbon atoms, in represents an integer of 1 to 3, and n's each independently represent an integer of 1 to 4, provided that at least one n represents an integer of 2 to 4, and at least one specific structure represented by the formula (1a) is present in the formula;

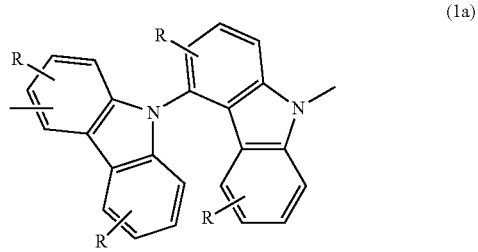

(1a)

where R's each have the same meaning as that in the general formula (1).

2. An organic electroluminescent device according to claim 1, wherein in the general formula (1), m represents art integer of 1 or 2, n's each independently represent an integer of 1 to 3, and at least one n represents an integer of 2 or 3.

3. An organic electroluminescent device according to claim 2, wherein in the general formula (1) all specific structures between carbazole rings comprise specific structures represented by the formula (1a) or by the formula (1a) and the following formula (1b):

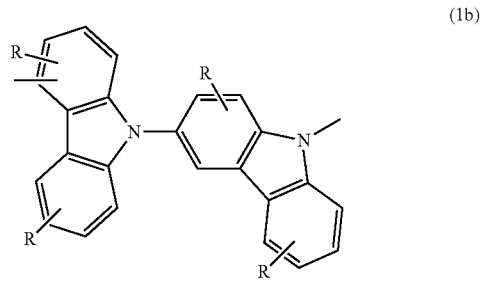

(1b)

where R's each have the same meaning as that in the formula (1a).

4. An organic electroluminescent device according to claim 1, wherein in the general formula (1), L represents an m-valent group produced by removing m hydrogen atoms from any one of the formulae (2) to (5):

(2)

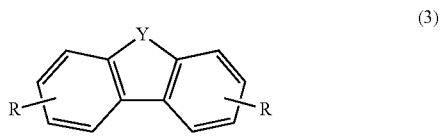

(3)

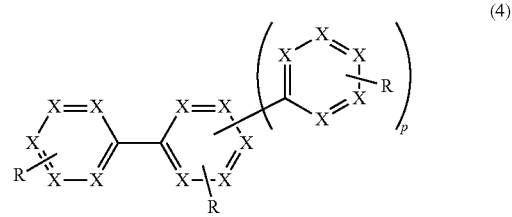

(4)

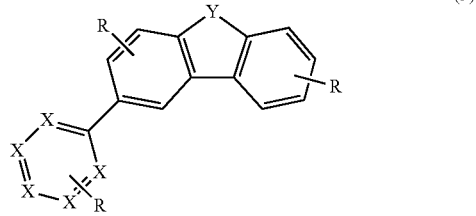

(5)

in the formulae (2) to (5), X's each independently represent CH or nitrogen and R's each independently represent hydrogen, an alkyl group having 1 to 10 carbon atoms, or a cycloalkyl group having 3 to 11 carbon atoms, in each of the formulae (3) and (5), Y represents oxygen or sulfur, and in the formula (4), p represents an integer of 0 to 2.

5. An organic electroluminescent device according to claim 4, wherein in the general formula (1), L represents an m-valent group produced by removing m hydrogen atoms from any one of the formulae (2) to (4).

6. An organic electroluminescent device according to claim 1, wherein in the general formula (1), a sum of n's is an integer of 2 to 6.

7. An organic electroluminescent device according to claim 1, wherein the organic layer containing the carbazole compound is an emitting layer containing a phosphorescent light-emitting dopant.

8. An organic electroluminescent device according to claim 3, wherein the organic layer containing the carbazole compound is an emitting layer containing a phosphorescent light-emitting dopant.

9. An organic electroluminescent device according to claim 4, wherein the organic layer containing the carbazole compound is an emitting layer containing a phosphorescent light-emitting dopant.

* * * * *